US007235523B2

(12) United States Patent
Waltz et al.

(10) Patent No.: US 7,235,523 B2
(45) Date of Patent: Jun. 26, 2007

(54) METHODS FOR THE TREATMENT OF HEPATIC DISORDERS

(75) Inventors: Susan E. Waltz, Loveland, OH (US); Mike A. Leonis, Norwood, OH (US); Sandra J. Degen, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 10/123,036

(22) Filed: Apr. 15, 2002

(65) Prior Publication Data

US 2003/0073656 A1  Apr. 17, 2003

Related U.S. Application Data

(60) Provisional application No. 60/283,788, filed on Apr. 13, 2001.

(51) Int. Cl.
*A61K 38/00* (2006.01)
*A61K 38/18* (2006.01)
(52) U.S. Cl. .................. 514/2; 424/143.1; 514/15
(58) Field of Classification Search ............. 435/69.5, 435/69.1, 69.6, 252.3, 360; 536/23.1, 24.1; 514/44, 2
See application file for complete search history.

(56) References Cited

U.S. PATENT DOCUMENTS

| | | | |
|---|---|---|---|
| 4,954,526 | A | 9/1990 | Keefer |
| 5,219,991 | A | 6/1993 | Leonard et al. |
| 5,278,192 | A | 1/1994 | Fung et al. |
| 5,315,000 | A | 5/1994 | Degen |
| 5,378,725 | A | 1/1995 | Bonjouklian et al. |
| 5,480,906 | A | 1/1996 | Creemer et al. |
| 5,504,103 | A | 4/1996 | Bonjouklian et al. |
| 5,527,685 | A | 6/1996 | Leonard et al. |
| 5,606,029 | A | 2/1997 | Degen |
| 5,696,086 | A | 12/1997 | Avraham et al. |
| 5,814,308 | A | 9/1998 | Zhang |
| 5,874,306 | A | 2/1999 | Beattie et al. |
| 5,916,770 | A * | 6/1999 | Yoshikawa et al. |
| 5,948,892 | A | 9/1999 | Wahl |
| 6,030,949 | A | 2/2000 | Comoglio et al. |
| 6,245,754 | B1 | 6/2001 | Kozikowski et al. |
| 6,248,560 | B1 | 6/2001 | Wahl |
| 2003/0212256 | A1 * | 11/2003 | Edinger et al. ............. 530/350 |

FOREIGN PATENT DOCUMENTS

WO     WO 98/55141    *  6/1998

OTHER PUBLICATIONS

Wang et al. Regulation of the RON Receptor Tyrosine Kinase Expression in Macrophages: Blocking the RON Gene Transcription by Endotoxin-In duced Nitric Oxide. Journal of Immunology, 2000 vol. 164:3815-3821.*

Leonard et al. Macrophage Stimulating Protein. Advances in Cancer Research, 2000 vol. 77:139-167.*
Branch, A. A Good Antisense is Hard to Find. TIBS, Feb. 1998 vol. 23, pp. 45-50.*
Crystal, RG. Transfer of Genes to Humans: Early Lessons and Obstacles to Success. Science, 1995 vol. 270:404-410.*
Anderson, WF. Human Gene Therapy. Nature, 1998 vol. 392 (6679 Suppl):25-30.*
Verma et al. Gene Therapy—Promises, problems and prospects. Nature, 1997 vol. 389:239-242.*
Rudinger J in Peptide Hormones. Editor Parsons JA. pp. 1-7, 1976, University Park Press, Baltimore.*
Bowie et al., 1990. Science, vol. 247, pp. 1306-1310. Deciphering the Message in Protein Sequences: Tolerance to Amino Acid Substitutions.*
Ngo et al., 1994. Computational Complexity, Protein Structure Prediction, and the Levinthal Paradox. The Protein Folding Problem and Tertiary Structure Prediction.*
Cirrhosis of the Liver. National Digestive Diseases Information Clearinghouse (NIDDIC website: digestive.niddk.nih.gove/ddiseases/pubs/cirrhosis; accessed May 30, 2006; 7 pages.*
Definition of Hepatobiliary. MedicineNet.com; medterms.com; accessed May 30, 2006; 1 page.*
Feng et al., Science in China Series C Life Sciences; 1999, 42; 5: 548-553.*
Bezerra et al, Are Hepatocyte Growth Factor-like Protein and Macrophage Stimulating Protein the Same Protein?. 1999 *Protein Science* 2, 666-668.
Chen, Y.-Q. et al, Activation of the RON Receptor Tyrosine kinase Inhibits Inducible Nitric Oxide Synthase (iNOS) Expression by Murine Peritoneal Exudate Macrophages: Phosphatidylinositol-3 Kinase is Required for RON-Mediated Inhibition of iNOS Expression,. 1998 *J. Immunol.* 161:4950-4959.
Correll, P. H. et al., Dergulated Inflammatory Response in Mice Lacking the STK/RON Receptor Tyrosine Kinase, 1997 *Genes Funct.* 1:69-83.
Follenzi, A., et al., Cross-talk Between the Proto-Oncogenes Met and Ron, 2000 *Oncogene* 19:3041-3049.
Gaudino, G., et al., The Prot-oncogene RON is Involved in Development of Epithelial, Bone and Neuro-endocrine Tissues, 1995 *Oncogene* 11:2627.
Han et al., Characterization of the DNF15S2 Locus on Human Chromosome 3: Identification of a Gene Coding for Four Kringle Domains with Homology to Hepatocyte Growth Factor, 1991 *Biochemistry* 30, 9768-9780.

(Continued)

*Primary Examiner*—Elizabeth Kemmerer
*Assistant Examiner*—Christina Borgeest
(74) *Attorney, Agent, or Firm*—Frost Brown Todd LLC

(57) ABSTRACT

The present invention relates to the prevention and treatment of injury and diseases to the liver, biliary tract, bile ducts, gall bladder and related hepatobiliary system. Specifically, the present invention relates to methods for decreasing the action of the RON receptor tyrosine kinase in liver physiology. More specifically, the present invention relates to the use of analogs and antagonists and antibodies for inhibiting the action of the RON receptor tyrosine kinase for the prevention and treatment of liver injury or damage in acute and chronic clinical conditions.

20 Claims, No Drawings

OTHER PUBLICATIONS

Leonard, E. J. and Danilkovitch, A., Macrophage Stimulating Protein, 2000 *Adv. Cancer Res.* 77:139-167.

McDowell, S. A., et al., The Role of the Receptor Tyrosine Kinase Ron in Nickel-Induced Acute Lung Injury, 2002 *Am. J. Respir. Cell Mol. Biol.* 26:99-104.

Mera, A. et al., Induction of Cell Shape Changes Through Activation of the Interleukin-3 Common β Chain Receptor by the RON Receptor-type Tyrosine Kinase, 1999 *J. Biol. Chem.* 274:15766-15774.

Muraoka, R. S. et al., the Ron/STK Receptor Tyrosine Kinase is Essential for Peri-implantation Development in the Mouse, 1999 *J. Clin. Invest.* 103:1277-1285.

Persons, D. A., et al., Fv2 Encodes a Truncated Form of the Stk Receptor Tyrosine Kinase, 1999 *Nat. Genet.* 23:159-165.

Ronsin, C. et al., A Novel Putative Receptor Protein Tyrosine Kinase of the MET Family, 1993 *Oncogene* 5: 1195-1202.

Saavedra, J. E., et al., Targeting Nitric Oxide (NO) Delivery in Vivo. Design of a Liver-Selective NO Donor Prodrug that Blocks Tumor Necrosis Factor-a-Induced Apoptosis and Toxicity in the Liver, 1997, *J. Med. Chem.* 40:1947-1954.

Torok, N. J. et al., Nitric Oxide Inhibits Apoptosis Downstream of Cyrochrome C Release, 2000 *Hepatology* 32:332A.

Wang, M.-H., et al., Macrophage-stimulating Protein Inhibits Induction of Nitric Oxide Production by Endotoxin- or Cytokine-stimulated Mouse Macrophages, 1994 *J. Biol. Chem.* 269:14027.

Wang, M.-H., et al., Requirement of Phosphatidylinositol-3 Kinase of Epithelial Cell Migration Activated by Human Macrophage Stimulating Protein, 1996 *Oncogene* 13, 2167-2175.

Wang, Ming-Hai, et al., *Macrophage Stimulating Protein (MSP) Binds to Its Receptor via the MSP β Chain*, Journal of Biological Chemistry, 272:27, pp. 16999-17004 (1997).

Waltz, Susan, et al., *Functional Characterization of Domains contained in Hepatocyte Growth Factor-like Protein*, Journal of Biological Chemistry, 272:48, pp. 30526-30537 (1997).

Waltz, Susan, et al., *Ron-mediated cytoplasmic signaling is dispensable for viability but is required to limit inflammatory responses*, Journal of Clin. Investigation 108:4, pp. 567-576 (Aug. 2001).

Kaplowitz, Neil; "Hepatology Highlights," *Liver Biology Biology and Pathology Editor*, pp. 1037-1038.

Leonis, Mike A.; Toney-Early, Kenya; Degen, Sandra J. F.; and Waltz, Susan E.; Deletion of the Ron Receptior Tyrosine Kinase Domain in Mice Provides Protection From Endotoxin-Induced Acute Liver Failure, *HEPATOLOGY*, Nov. 2002: 1053-1060.

Rao, R.K.; Seth, A; and Sheth, P.; "Recent Advances in Alcoholic Liver Disease I. Role of intestinal permeability and endotoxemia in alcoholic liver disease," *American Journal of Physiology—Gastrointestinal and Liver Physiology*, 286: G881-G884, © 2004; (information current as of Apr. 27, 2005).

* cited by examiner

METHODS FOR THE TREATMENT OF HEPATIC DISORDERS

This application claims the benefit of U.S. Provisional Patent Application Ser. No. 60/283,788, filed Apr. 13, 2001, which application is hereby incorporated by reference in its entirety.

This invention was made in part with Government support under one or more grants including Grant Nos. R01 HD36888, R01DK47003 and T32 DK07727, awarded by the National Institutes of Health. The Government may have certain rights in this invention.

BACKGROUND OF THE INVENTION

The present invention relates to the prevention and treatment of injury and diseases to the liver, biliary tract, bile ducts, gall bladder and related hepatobiliary system. Specifically, the present invention relates to methods for decreasing the action of the RON receptor tyrosine kinase in liver physiology. More specifically, the present invention relates to the use of analogs and antagonists and antibodies for inhibiting the action of the RON receptor tyrosine kinase for the prevention and treatment of liver injury or damage in acute and chronic clinical conditions.

Liver damage may occur in a number of acute and chronic clinical conditions including drug-induced hepatotoxicity, viral infections, vascular injury, autoimmune disease, metabolic disease and blunt trauma.

Acute liver failure comprises a group of severe liver disease with a variety of both known and unknown causative agents. Known potential precipitating agents, for example, include drugs and toxins (e.g. acetaminophen and Amanita mushroom poisoning); viruses (e.g. hepatitis B virus and Epstein Barr virus), and autoimmune hepatitis. Genetic background and/or the presence of underlying liver disease (e.g. preexisting alcoholic steatohepatitis and/or α1-antitrypsin disease) may contribute to the disease process.

At present, there is only one direct therapy for any of the multiple causes of acute liver failure (i.e., the use of N-acetylcysteine in the case of acetaminophen toxicity), and this therapy has not been broadly applicable to other causes of acute liver failure. Supportive care is the mainstay of therapy for most patients. Mortality in adults for all causes of acute liver failure taken together is >60% (even higher in children); the remaining patients progress to orthotopic liver transplantation or, rarely, recover on their own. Few useful markers exist that predict the presence and clinical course of disease, and additional specific therapies to alter the progression of acute liver failure have not been forthcoming (Lee, W. M., (1999) Chapter 35, in Schiff's Diseases of the Liver, 8:879–905).

The pathogenesis of acute liver failure in humans is poorly understood, but an initial understanding is emerging. Kupffer cells (the resident macrophage of the liver) play a prominent role in the disease process, with the release of cytokines and generation of proinflammatory mediators such as tumor necrosis factor α (TNFα) and nitric oxide (NO), both of which can negatively impact the hepatocyte and biliary tree. Endotoxemia is frequent and likely contributes to the activation of Kupffer cells in human disease. (Lee, W. M., (1999), see above). TNFα has been found to be a key mediator of both human and murine forms of acute liver failure (Muto, Y. et al. (1988) Lancet 2:72–74), and expression of TNFα by infiltrating mononuclear cells is associated with increased amounts of apoptotic hepatocytes in acute liver failure (Streetz, K. et al. (2000) Gastroenterol. 119:449–460).

Hepatocyte growth factor-like protein ("HGFL"), also known as macrophage stimulating protein ("MSP"), is a heterodimeric, kringle-containing growth factor belonging to the hepatocyte growth factor family (Bezerra et al. (1999) Protein Science 2, 666–668). HGFL has been found to bind and activate a receptor comprising a heterodimeric transmembrane glycoprotein referred to as "p185RON" or "RON" or stem cell-derived tyrosine kinase. HGFL binds to the RON receptor, which is a tyrosine kinase receptor encoded for by the RON gene (Gaudino, G., et al, (1995) Oncogene 11:2627). Functional characterization of the four kringle and putative non-enzymatically active serine protease-like domains within HGFL/MSP has been performed (Waltz, S. E. et al. (1997) J. Biol. Chem. 272:30256–30537; Wang, M. -H. et al. (1997) J. Biol. Chem. 272:16999–17004). These results suggest that the C-terminal serine protease-like domain (or β chain) of HGFL is required for binding to the RON receptor, and the kringle regions, especially kringle domains 2 and 3, are required for biological function of the HGFL/RON receptor interaction. The majority of mRNA coding for HGFL is expressed in the liver. It is also expressed, at lower levels, in other tissues including the lung, adrenals and placenta. To date, the physiological roles of HGFL in the body have not been fully understood.

Binding of HGFL ligand to RON receptor is expected to lead to receptor homodimerization, thus activating the receptor's tyrosine kinase activity and leading to cross autophosphorylation of tyrosine residues on the adjoining cytoplasmic chain. Phosphorylation of RON receptor then leads to recruitment of SH2-containing effector molecules, such as phospholipase C-γ and phosphatidylinositol-3-kinase (PI-3-kinase; for review see, Leonard, E. J. and Danilkovitch, A. 2000, Adv. Cancer Res. 77, 139–167). Heterodimerization of RON receptor with other tyrosine kinase receptors, such as the Met and erythropoietin receptors, as well as GM-CSF and the common β signal transducer that associates with interleukins-3 and -5, has also become increasingly obvious, and implies multiple roles, and avenues for RON receptor activation (Persons, D. A., et al. (1999) Nat. Genet. 23:159–165; Follenzi, A., et al. (2000) Oncogene 19:3041–3049; Mera, A. et al. (1999) J. Biol. Chem. 274:15766–15774).

A number of biological functions have been described for this ligand/receptor pair, including activation and differentiation of resident peritoneal macrophages (Iwama, A., et al. (1995) Blood 86:3394), inhibition of inducible nitric oxide synthase (iNOS) expression in endotoxin and cytokine-stimulated macrophages (Wang, M. -H., et al. (1994) J. Biol. Chem. 269:14027; Correll, P. H. et al, (1997) Genes Funct. 1:69–83; Muraoka, R. S. et al. (1999) J. Clin. Invest. 103:1277–1285; Waltz, S. E. et al. (2001), J. Clin. Invest. 108, 567–576), and stimulation of proliferation of certain epithelial cell lines and activation of PI-3-kinase activity (Leonard, E. J. and Danilkovitch, A. (2000) Adv. Cancer Res. 77:139–167).

RON activation by HGFL transduces inhibitory signals that block LPS- and IFNγ-induced iNOS expression. RON-mediated inhibition of iNOS expression in macrophages is effected by PI-3-kinase, as illustrated by the effects of transfection of a dominant-inhibitory PI-3-kinase p85 subunit and/or the addition of wortmannin, a specific inhibitor of PI-3-kinase to the response of macrophage to lipopolysaccharide (LPS or endotoxin) and interferon γ (Chen, Y. -Q. et al. (1998) *J. Immunol.* 161:4950–4959).

Nitric oxide generation occurs in several models of acute liver injury and elevated hepatocellular NO levels can inhibit liver damage in a variety of experimental liver injury models, possibly via inhibition of caspase activities (Torok, N. J. et al., (2000) *Hepatology* 32:332A, which play key roles in the development of cellular apoptosis. For example, administration of liver-specific NO donors, such as v-PYRRO (Saavedra, J. E., et al. (1997), *J. Med. Chem.* 40:1947–1954) can markedly blunt the progression of TNFα-induced murine acute liver failure.

The present invention shows that gene-targeted mice lacking the tyrosine kinase-containing cytoplasmic domain of the RON receptor have dramatically altered physiological responses compared to control mice possessing wild type RON receptor. These tyrosine kinase deficient ($TK^{-/-}$) mice have enhanced lethality to otherwise nontoxic doses of LPS, and macrophage isolated from $TK^{-/-}$ mice have enhanced production of nitric oxide in response to LPS and interferon γ. Dramatic differences in the inflammatory responses in lung and skin injury models have also been noted between control and $TK^{-/-}$ mice (see Waltz, S. E. et al., (2001), J. Clin. Invest. 108, 567–576; McDowell, S. A., et al. (2002) *Am. J. Respir. Cell Mol. Biol.* 26:99–104).

Little is known about the involvement of the RON receptor in liver physiology, except that it is present in liver tissue.

The present invention now provides for the pharmacological blockage of the hepatocyte growth factor-like protein ("HGFL") ligand/RON receptor interaction and/or blockage of RON receptor downstream signaling cascades for protective effects towards acute and chronic liver disease, and in particular, acute liver failure.

Therefore, it would be advantageous to have an effective therapy for the prevention and treatment of liver disease. This need exists in any patient population in which chronic or acute liver damage has been induced for example by hepatotoxic compounds, radiation exposure, viral infection, autoimmune disease, and where it is desirable to inhibit the progression of such damage. This need further exists in any patient population at risk of developing liver damage such as in the case of drug overdose, accidental exposure to infected blood samples, or in a clinical setting which includes aggressive chemotherapy, radiation therapy or liver transplantation.

STATEMENT OF THE INVENTION

The present invention provides for the prevention and treatment of injury and diseases to the liver, biliary tract, bile ducts, gall bladder and related hepatobiliary system. Specifically, the present invention relates to methods for decreasing the action of the RON receptor tyrosine kinase in liver physiology. More specifically, the present invention relates to the use of analogs and antagonists, antibodies and nucleic acid modifiers (e.g., ribozymes) for inhibiting the action of the RON receptor tyrosine kinase for the prevention and treatment of liver injury or damage in acute and chronic clinical conditions.

This invention concerns the use of 1) whole or truncated HGFL protein analogs, which are readily available, 2) HGFL blocking antibodies, 3) RON receptor blocking antibodies, 4) peptide fragments based on the sequences of the HGFL or RON receptor obtained from any species, 5) nonspecific or specific RON receptor tyrosine kinase activity inhibitors or 6) Ron receptor or HGFL nucleic acid inhibitors, e.g., single stranded DNA or RNA antisense molecules designed to interfere with the stability or translation of HGFL or RON receptor mRNA, or with the transcription from HGFL or RON receptor genomic DNA sequences, in pharmaceutical compositions for the treatment of any kind of impairment or degeneration of the hepatobiliary system of inflammatory, infectious or drug/toxin-induced origin, including but not limited to pathologic states leading to apoptosis of hepatocytes. The use of these agents, either alone or in conjunction with nonspecific or liver-specific nitric oxide donors, may lead to improved outcomes in patients being treated for these pathologies, as measured by magnitude and/or duration of abnormal aminotransferase elevation, duration of treatment regimens, liver graft function or survival, or mortality.

The present invention is based on the experimental finding that inhibition of the RON tyrosine kinase receptor provides effective protection in an experimental model of acute liver injury, based on assessment of liver tissue necrosis and elevated serum transaminase levels, both indicative of liver damage.

The present invention relates to methods for the prevention or treatment of the progression of liver damage in a patient at risk of developing or having been diagnosed with liver damage comprising administering to the patient a preventatively effective amount of a RON receptor-inhibiting compound. The patient preferably is mammalian, more preferably human.

In another embodiment, the invention relates to a method for the treatment of a patient with a hepatoprotective therapeutic agent effective in the prevention or treatment of a disorder or pathophysiological condition comprising (a) administering to said patient simultaneously or in optional order (1) a biologically effective dose of said therapeutic agent and (2) a preventatively effective amount of RON receptor inhibiting agent and (b) monitoring said patient for indication of liver damage and (c) continuing said treatment until the disorder or condition is eliminated or until liver damage is improved.

In another embodiment, the present invention relates to a method for the prevention of the establishment of liver damage in a patient at risk for developing liver damage comprising administering to said patient a liver damage preventative amount of RON receptor inhibiting compound.

In one embodiment, the RON receptor-inhibiting compound is an HGFL analog. In another embodiment, the RON receptor-blocking compound is a RON receptor tyrosine kinase antagonist. In another embodiment, the RON receptor-blocking agent is an antibody directed towards the RON receptor in which the binding of the antibody with the RON receptor prevents normal activation of the RON receptor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

In the description that follows, a number of terms used in the art are extensively utilized. In order to provide a clear and consistent understanding of the specification and claims, including the scope to be given such terms, the following definitions are provided:

"Acute liver injury" refers to liver injury of rapid onset (<6 weeks duration from time of onset of symptoms, such as jaundice, to presentation) leading to abnormal serum alanine aminotransferase levels, or abnormal conjugated bilirubin levels.

"Acute liver failure" (also known as fulminant hepatic failure) is the umbrella term for liver failure which occurs within 12 weeks of the onset of jaundice (based on O'Grady et al. (1993), Lancet 342:273–275). This encompasses acute liver injury, but in addition, includes the presence of abnormal liver synthetic function, as measured by serum albumin level or prothrombin time, with or without the presence of clinical ascites or hepatic encephalopathy.

"Alteration", "amino acid alteration", "variant" and "amino acid sequence variant" as used herein refer to HGFL molecules with some differences in their amino acid sequences as compared to a native HGFL, such as to native human HGFL. Ordinarily, the variants will possess at least about 80% homology with those domains of wild-type (human) HGFL that are retained in their structure, and preferably, they will be at least about 90% homologous with such domains. Amino acid sequence variants of HGFL polypeptides for use as RON receptor inhibitors or HGFL antagonists may be predetermined mutant forms made by mutating the DNA, either to arrive to an allele or a variant not found in nature, provided that such variants maintain, in part, the biological activity in kind of native human HGFL. Such mutations typically involve substitution, deletion and/or insertion of one or more amino acids in the native amino acid sequence. The amino acid changes also may result in further modifications of HGFL upon expression in recombinant hosts, e.g. introducing or moving sites of glycosylation.

"Ameliorate" or "amelioration" means a lessening of the detrimental effect or severity of the hepatobiliary damage in the subject receiving therapy, the severity of the response being determined by means that are well known in the art.

"Antagonist" or "antagonistic" when used herein refer to or describe a molecule which is capable of directly or indirectly substantially counter-acting, reducing or inhibiting HGFL biological activity or RON receptor activation.

"Antibody" is used herein in a broad sense and includes intact immunoglobulin molecules and immunoglobulin fragments (such as Fab, F(ab')2, or Fv), so long as they exhibit any of the desired RON receptor inhibiting properties or HGFL antagonistic properties described herein. Antibodies are typically proteins that exhibit binding specificity to a specific antigen. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity. See U.S. Pat. No. 4,816,567; incorporated herein by reference in its entirety.

"Growth factor" as used herein refers to those factors required to regulate developmental events or required to regulate expression of genes encoding other secreted proteins that may participate in intercellular communication and coordination of development and includes, but is not limited to, insulin-like growth factor-I and II (IGF-I and II), epidermal growth factor (EGF), type a and type b transforming growth factor (TGF-alpha and TGF-beta), nerve growth factor (NGF), fibroblast growth factor (FGF), platelet-derived growth factor (PDGF), sarcoma growth factor (SGF), granulocyte macrophage colony stimulating growth factor (GM-CSF), vascular endothelial growth factor (VEGF), hemopoietic growth factors erythropoietin (EPO), granulocyte colony stimulating factor (G-CSF), megakaryocyte growth and differentiation factor (MGDF), acidic and basic fibroblast growth factor (FGF), keratinocyte growth factor (KGF), erythropoietin (EPO), stem cell factor (SCF), interleukins (such as interleukin-1, interleukin-2, interleukin-3, interleukin-4, interleukin-5, interleukin-6, interleukin-7, interleukin-8, interleukin-9, interleukin-10, interleukin-11, interleukin-12), interferon gamma (Inf-gamma), tumor necrosis factor alpha (TNF-alpha), brain-derived neurotrophic factor (BDNF), neurotrophin 3 (NT3), or neurotrophin 4/5 (NT4/5), ciliary neurotrophic growth factor (CNTF), leukemia inhibitory factor (LIF) and oncostatin.

"Hepatobiliary system" refers to the liver and its vessels, as well as the biliary tract, including the intra- and extra-hepatic bile ducts and gall bladder.

"HGFL" refers to hepatocyte growth factor-like protein, also known as macrophage stimulating protein ("MSP"). As used herein, the terms "macrophage stimulating protein" and "HGFL" refer to a growth factor, which typically has a structure comprising four kringle domains. The terms "hepatocyte growth factor-like protein" and "HGFL" refer to the mature, pre, pre-pro, and pro forms of the protein, either purified from a natural source, chemically synthesized or recombinantly produced. The HGFL protein may be in a single chain form or heterodimeric form. The present definition specifically includes HGFL encoded by the sequence published by Han et al. (1991) Biochemistry 30, 9768–9780. (available from EMBL/GenBank/DDBJ under accession number M74178; the nucleotide and amino acid sequence also being provided herein in the SEQUENCE LISTING as SEQ ID NO: 1 and SEQ ID NO: 2, respectively) as well as those described in U.S. Pat. Nos. 5,606,029 and 5,315,000, each of which is incorporated herein by reference in their entirety. Methods for isolating and purifying HGFL are well known in the art. See, for example, U.S. Pat. Nos. 6,248,560, 5,948,892, 5,916,770, 5,874,306, 5,814,308, 5,606,029, 5,315,000, 5,696,086 and 5,219,991, incorporated herein by reference in their entirety.

"HGFL antagonist" refers to any molecule that inhibits the activity of HGFL in causing activation of the RON receptor tyrosine kinase. Specifically, the term HGFL antagonist refers to any molecule that inhibits the activity of the RON receptor in causing liver damage or death of hepatocytes. Typically the HGFL antagonist is a protein that binds to the HGFL-binding site on the RON receptor. In addition, the antagonist may be a non-proteineacious small molecule that acts as a HGFL antagonist. Such molecules can be screened by their ability to inhibit the action of HGFL on the RON receptor and more specifically their ability to inhibit the action of HGFL in promoting liver damage or liver cell death using assays well known in the art.

"HGFL biological activity" when used herein refers to any mitogenic, motogenic or morphogenic activities of HGFL or any activities, including modulation of inflammatory responses, occurring as a result of HGFL binding to a RON receptor. HGFL biological activity may, for example, be determined in an in vitro or in vivo assay of hepatocyte growth promotion. Adult rat hepatocytes in primary culture have been used to test the effect of HGFL on hepatocyte proliferation. Accordingly, the effect of a HGFL antagonist can be determined in an assay suitable for testing the ability of HGFL to induce DNA synthesis of rat hepatocytes in primary cultures. Human hepatocytes can be cultured similarly to the methods established for preparing primary cultures of normal rat hepatocytes. Alternatively, the effect of a HGFL antagonist can be determined in an assay suitable for testing the ability of HGFL to induce DNA synthesis in other types of cells expressing RON receptor(s), such as lung cells or epithelial cells. The effect of HGFL antagonists can also be tested in vivo in animal models.

"HGFL truncated proteins" or "analogs" refers to HGFL-derived proteins lacking parts of the HGFL protein sequence or carbohydrate structure, either generated from recombinant DNA-based technologies, or originating from intact whole HGFL isolated from any mammalian source.

"Liver damage" is used herein in the broadest sense, and indicates any structural or functional liver injury resulting, directly or indirectly, from internal or external factors or their combinations. Liver damage can be induced by a number of factors including, but not limited to, exposure to hepatotoxic compounds, chronic ethanol exposure, radiation exposure, mechanical liver injuries, genetic predisposition, viral infections, autoimmune disease, or transplantation-related liver damage (including acute and chronic cellular rejection).

Liver damage induced by hepatotoxic compounds includes direct cytotoxicity including drug hypersensitivity reactions, cholestasis, and injury to the vascular endothelium. A number of hepatotoxic compounds, including certain therapeutics, induce cytotoxicity. Hepatotoxic compounds can produce liver cytotoxicity by direct chemical attack or by the production of a toxic metabolite. Although the exact mechanism of hepatotoxicity is uncertain, the products of metabolism are highly reactive species that bind to cellular macromolecules and cause lipid peroxidation and inactivation of drug metabolizing and other enzymes. Those drugs inducing cytotoxicity by direct chemical attack include the following: anesthetics, neuropsychotropics, anticonvulsants, analgesics, hormones, antimicrobials, cardiovascular drugs, immunosuppressives and antineoplastics. Drugs can produce vascular lesions of the liver, including thrombosis of the hepatic veins, occlusion of the hepatic venules or veno occlusive disease (VOD), and peliosis hepatitis, in addition, lesions including sinusoidal dilation, perisinusoidal fibrosis, and hepatoportal sclerosis can occur.

Liver damage, whether caused by the hepatotoxicity of a compound, radiation therapy, genetic predisposition, mechanical injury or any combination of such and other factors, can be detected by several means. Biochemical tests have been used clinically for many years as the standard measure of hepatotoxicity. Most biochemical tests generally fall into two categories: tests which measure specific liver markers, for example, prothrombin clotting time, and/or hepatic blood flow, or tests which analyze serum markers, for detection of necrosis, cholestasis, progressive fibrogenesis, or hepatoma. In many patients, computed tomography (CT), ultrasound, scintiscans, or liver biopsy may be needed to determine the nature of the liver disease.

"Nitric oxide (NO) stimulator" means an agent that acts to produce increased levels of NO. Preferably, the nitric oxide stimulator is a one or more agents selected from the group consisting of nitric oxide donors, NO synthase (NOS) stimulators, and NO catabolism inhibitors. Suitable NO donors include, but are not limited to, nitroglycerin, amyl nitrate, nitroprusside, isosorbide dinitrate, erythityl dinitrate, non-oates and pentaerythritol tetranitrate. Preferably, the nitric oxide donor is sodium nitroprusside, nitroglycerin, SIN-1, isosorbid mononitrate or isosorbid dinitrate. Suitable NOS stimulators include, but are not limited to, bradykinin, acetylcholine, thrombin, histamine and substance P. Suitable NO catabolism inhibitors include antioxidants, such as, but not limited to, ascorbate, tocopherol and beta-carotene. The nitric oxide synthase substrate is generally L-arginine.

The term "patient" includes those patients who are anticipated to be exposed to or have been exposed to any factor known to have the potential of inducing liver damage. The definition further includes actual or potential sustained liver injury through physical trauma. Patients at risk of developing liver damage include those patients having genetic metabolic disorders and who are genetically predisposed to induction of liver damage.

"Prevention" as used herein includes the complete or partial blocking of the occurrence of anticipated liver damage and the interception or moderation of the progression of liver damage already initiated. Preferably, existing liver damage is completely or partially reversed but prevention, as used herein, also refers to any amelioration of effects.

"Protein" and "polypeptide" mean any chain of amino acid residues, regardless of length or post-translational modification (e.g., glycosylation or phosphorylation). The polypeptide growth factors useful in the invention are referred to as "substantially pure," meaning that a composition containing the polypeptide is at least 60% by weight (dry weight) the polypeptide of interest, e.g., a HGFL antagonist polypeptide. Preferably, the polypeptide composition is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis.

"RON", "RON receptor", or "p185RON", refer to the RON receptor tyrosine kinase, also known as the stem cell-derived tyrosine kinase ("STK"). This glycoprotein has two polypeptide chains linked by disulfide bonds: the beta (150 kDa) and alpha (35 kDa) chains. p185RON is synthesized as a single chain precursor, which is subsequently converted into a mature, heterodimeric form by proteolytic cleavage. The RON cDNA encodes a protein of 1,400 amino acids that shares an overall similarity to the HGF receptor structurally and has about 63% sequence identity in the catalytic domain. The present definition specifically includes receptor encoded by the sequence published by Ronsin, C. et al. (1993) Oncogene 5: 1195–1202 (available from EMBL/GenBank/DDBJ under accession number X70040; the nucleotide and amino acid sequence also being provided herein in the SEQUENCE LISTING as SEQ ID NO: 3 and SEQ ID NO: 4, respectively) as well as those described in U.S. Pat. Nos. 5,606,029 and 5,315,000, each of which is incorporated herein by reference in their entirety. Methods for isolating and purifying HGFL are well known in the art.

"RON receptor activation" refers to RON receptor dimerization or RON receptor-induced tyrosine kinase activity. RON receptor activation may occur as a result of HGFL binding to a RON receptor, but may alternatively occur independently of any HGFL binding to a RON receptor.

"RON receptor antagonist" refers to any molecule that inhibits the activity of the RON receptor in causing liver damage or death of hepatocytes by a) interfering with the binding of ligand, including but not limited to hepatocyte growth factor like protein, b) interfering with the functional activity of the RON receptor, or c) interfering with the receptor homo-or hetero-dimerization with another protein receptor tyrosine kinase(s).

"RON receptor blocking antibodies" refers to any polyclonal, monoclonal (or Fab fragment derived from said monoclonal or polyclonal antibody) or chimeric antibody (i.e. having at least one domain of murine origin and at least one domain of human origin), which binds to the RON receptor and: a) inhibits binding of ligand, including but not limited to hepatocyte growth factor like protein, b) inhibits functional activity of the RON receptor, or c) inhibits receptor homo-or hetero-dimerization with another protein receptor tyrosine kinase(s).

"RON receptor inhibitor" refers to a therapeutic agent capable of decreasing the RON receptor activation including, without limitation, where such agent: a) inhibits binding of ligand, including but not limited to hepatocyte growth factor like protein, b) inhibits functional activity of the RON receptor, or c) inhibits receptor homo-or hetero-dimerization with another protein receptor tyrosine kinase(s).

"Therapeutically effective amount" means that the amount of RON receptor inhibitor used for administration is sufficient to ameliorate the clinical symptoms of liver damage or to otherwise reduce the severity of or prevent further liver damage. Therapeutically effective amounts will differ based upon the nature of the patient, the degree and severity of the disease, the clinical setting, the mode of administration, and the like and can be deterned empirically by the skilled practitioner without undue experimentation.

"Therapeutic" as used herein refers to those agents effective in the prevention or treatment of a disorder or pathologic physiological condition.

"Treat," "treating," "treatment," and "therapy" as used herein refer to any curative therapy, prophylactic therapy, ameliorative therapy and preventative therapy.

In one embodiment, the RON receptor inhibitor is a protein that comprises an amino acid sequence with least about 65% sequence homology, and more preferably at least about 75% sequence homology with the amino acid sequence coded for by one or more of the oligonucleotide sequences shown in the sequences of SEQ ID NO: 1 and SEQ ID NO: 3. In another embodiment, the RON receptor inhibitor is a protein that comprises an amino acid sequence with least about 65% sequence homology, and more preferably at least about 75% sequence homology with the amino acid sequences shown in the sequences of SEQ ID NO: 2 and SEQ ID NO: 4.

In another embodiment, the RON receptor inhibitor comprises HGFL variants and fragments without substantial HGFL biological activity and RON receptor variants and fragments which interfere with the action of HGFL wherein the inhibitor is a polypeptide comprising an amino acid sequence at least 6 amino acids in length that includes at least 4 contiguous amino acids of a sequence coded for by one or more of the oligonucleotide sequences shown in SEQ ID NO: 1 and SEQ ID NO: 3, and retains its abilities as a RON receptor inhibitor. Preferable, the sequence at least 10 amino acids in length, more preferably at least 20 amino acids in length. Preferably, the sequence contains at least 6 contiguous amino acids, more preferably at least 9 contiguous amino acids of a sequence coded for by one or more of the oligonucleotide sequences shown in SEQ ID NO: 1 and SEQ ID NO: 3. Generally, the sequence is no more than 200 amino acids in length, preferably no more than 100 amino acids in length.

In another embodiment, the RON receptor inhibitor comprises HGFL variants and fragments without substantial HGFL biological activity and Ron receptor variants and fragments which inhibit HGFL biological activity wherein the inhibitor is a polypeptide comprising an amino acid sequence at least 6 amino acids in length that includes at least 4 contiguous amino acids of a polypeptide sequence shown in SEQ ID NO: 2 and SEQ ID NO: 4, which retains its abilities as a RON receptor inhibitor.

In another embodiment, the RON receptor inhibitor comprises HGFL variants and fragments without substantial HGFL biological activity wherein the inhibitor is a polypeptide comprising an amino acid sequence at least 6 amino acids in length that includes at least 4 contiguous amino acids of a sequence coded for by one or more of the mutant HGFL oligonucleotide sequences selected from the group consisting of ΔPAP, ΔK1, ΔK2, ΔK, ΔK4, ΔK1K2, ΔL, K1K2, Glu, Xa, IIa, and 48G, which retains its abilities as a RON receptor inhibitor.

One aspect of the invention pertains to isolated HGFL proteins, and portions thereof, or derivatives, fragments, analogs or homologs thereof which interfere with the RON receptor activity. The present invention also provides for fusion polypeptides, comprising HGFL polypeptides and fragments. Homologous polypeptides may be fusions between two or more HGFL polypeptide sequences or between the sequences of HGFL and a related protein. Fusion partners include immunoglobulins, bacterial beta-galactosidase, trpE, protein A, β-lactamase, alpha amylase, alcohol dehydrogenase and yeast alpha mating factor.

Fragments provided herein are defined as sequences of at least 4 (contiguous) amino acids, a length sufficient to allow for specific recognition of an epitope and are at most some portion less than a full length sequence. Fragments may be derived from any contiguous portion of an amino acid sequence of choice. Derivatives are amino acid sequences formed from the native compounds either directly or by modification or partial substitution. Analogs are amino acid sequences that have a structure similar to, but not identical to, the native compound but differ from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified amino acid, as described below. Derivatives or analogs of the proteins of the invention include, but are not limited to, molecules comprising regions that are substantially homologous to the proteins of the invention, in various embodiments, by at least about 70%, 80%, 85%, 90%, 95%, 98%, or even 99% identity (with a preferred identity of 80–99%) over an amino acid sequence of identical size.

The HGFL analogs and antagonists useful in the practice of the present invention can be prepared in a number of ways. For instance, the HGFL antagonists can be prepared using an isolated or purified form of HGFL antagonists. Methods of isolating and purifying HGFL antagonists are known in the art. HGFL antagonists can be chemically synthesized and prepared using recombinant DNA techniques known in the art.

The HGFL antagonists may be from human or any non-human species. For instance, a mammal may have administered HGFL fragments from a different mammalian species (e.g., mice can be treated with human HGFL antagonists). There is substantial homology (about 81% amino acid identity) between mouse HGFL and human HGFL, and thus, it is expected that HGFL antagonists from different mammalian species can be employed. Preferably, however, the mammal is treated with homologous HGFL antagonists (e.g., humans are treated with human HGFL antagonists) to avoid potential immune reactions to the HGFL antagonists.

In a preferred embodiment of the invention, the RON receptor antagonists are provided. Non-limiting examples of RON receptor antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

In another embodiment of the invention, the RON receptor inhibitors include Ron receptor or HGFL nucleic acid inhibitors. Such Ron receptor or HGFL nucleic acid inhibitors include single stranded DNA or RNA antisense molecules designed to interfere with the stability or translation of HGFL or RON receptor mRNA, or with the transcription from HGFL or RON receptor genomic DNA sequences. Examples of such nucleic acid inhibitors include, but are not limited to, ribozymes (RNA species which serve as sequence-specific molecular scissors) or single-strand DNA species which may selectively inhibit the HGFL- or RON receptor-biological activity. Design of such molecules is familiar to those skilled in the art. (e.g. Bock L. et al. (1992) Nature 355, 564–566).

In another embodiment, the RON receptor antagonists of the invention are RON receptor antibodies. For instance, the antagonistic antibodies may be polyclonal antibodies. Methods of preparing polyclonal antibodies are known to those skilled in the art. One can raise polyclonal antibodies in a mammal, for example, or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants that may be employed include Freund's complete adjuvant and MPL-TDM adjuvant (monophosphoryl Lipid A, synthetic trehalose dicorynomycolate). One skilled in the art, without undue experimentation, may select the immunization protocol. The mammal can then be bled, and the serum assayed for RON receptor antibody titer. If desired, the mammal can be boosted until the antibody titer increases or plateaus.

The antagonistic antibodies of the invention may, alternatively, be monoclonal antibodies. Antagonistic monoclonal antibodies of the invention may be prepared using hybridoma methods well known in the art. In a hybridoma method, a mouse or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent may alternatively comprise a fragment or portion of HGFL or a RON receptor having one or more amino acid residues that participate in the binding of HGFL to its receptor.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma. Immortalized cell lines are usually transformed mammalian cells, particularly myeloma cells of rodent, bovine and human origin.

Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567, incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for a RON receptor and another antigen-combining site having specificity for a different antigen.

It is believed, however, that monovalent antibodies capable of binding to a RON receptor will be especially useful as RON receptor antagonists. Such monovalent antibodies may be directed against the HGFL binding site of the receptor or may otherwise be capable of interfering with HGFL, its fragments or its variants binding to the RON receptor, such as by sterically hindering HGFL, its fragments or its variants access to the receptor, or by binding HGFL itself. Alternatively, the monovalent antibodies may be capable of sterically preventing RON receptor dimerization.

Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In a preferred embodiment of the invention, the antagonists comprise Fab fragments of monoclonal antibodies specific for the RON receptor.

In a preferred embodiment of the invention, the RON receptor inhibitor, e.g., an antagonist, monoclonal antibody or fragment or analog thereof, will inhibit at least one of (a) RON receptor activation, (b) binding of HGFL, its fragments or its variants, or (c) HGFL biological activity at least by about 50%, preferably, greater than about 80%, and more preferably, greater than about 90%.

In addition to the antagonistic antibodies described above, it is contemplated that chimeric or hybrid antagonistic antibodies may be prepared in vitro using known methods in synthetic protein chemistry, including those involving crosslinking agents. The antagonistic antibodies of the invention may further comprise humanized antibodies or human antibodies. Methods for humanizing non-human antibodies are well known in the art. See U.S. Pat. No. 4,816,567), incorporated herein by reference in its entirety.

In another embodiment of the invention, methods for treating liver damage are provided. In the methods, RON receptor antagonist is administered to a mammal diagnosed as having liver damage. While the term "liver damage" as used herein is not limited to any one specific form of the disease, it is believed that the methods will be particularly effective for the treatment of pathologies of the hepatobiliary system of inflammatory, infectious, toxin, or liver graft preservation-induced origin. It is of course contemplated that the methods of the invention can be employed in combination with still other therapeutic techniques such as surgery and chemotherapy.

The RON receptor inhibitor is preferably administered to a mammal in a pharmaceutically acceptable carrier. Suitable carriers and their formulations are well known in the art. Typically, an appropriate amount of a pharmaceutically acceptable salt is used in the formulation to render the formulation isotonic. Examples of the pharmaceutically acceptable carrier include saline, Ringer's solution and dextrose solution. The pH of the solution is preferably from about 5 to about 8, and more preferably from about 7 to about 7.8. Further carriers include sustained release preparations such as semipermeable matrices of solid hydrophobic polymers containing the antagonist, which matrices are in the form of shaped articles, e.g., films, liposomes or microparticles. It will be apparent to those persons skilled in the art that certain carriers may be more preferable depending upon, for instance, the route of administration and concentration of RON receptor inhibitor being administered.

The RON receptor inhibitor or HGFL antagonist may be administered to a subject mammal, preferably human, via any of the accepted modes of administration for agents that exhibit such activity. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Effective dosages and schedules for administering the antagonist may be determined empirically, and making such determinations is within the skill in the art. Interspecies scaling of dosages can be performed in a manner known in the art. It is understood by those skilled in the art that the dose of RON receptor inhibitor that must be administered will vary depending on, for example, the mammal which will receive the RON receptor inhibitor, the nature of the medical condition or therapy believed to be responsible for liver injury or damage, the extent of damage to the tissues, the route of administration, and the identity of any other drugs being administered to the mammal. It is also understood that it may be necessary to give more than one dose of RON receptor inhibitor. Generally, multiple doses of RON receptor inhibitor will be required for administration. Administration of RON receptor inhibitor should be continued until acceptable liver function levels in the mammal are attained. Guidance in selecting appropriate doses for antibody antagonists is well known in the art.

The effect of the RON receptor inhibitors on hepatocyte growth and prevention of liver damage can also be tested in vivo in transgenic animal models such as described in U.S. Pat. No.5,087,571, incorporated herein by reference in its entirety.

In the aforementioned methods, the RON receptor inhibitor can alternatively be administered in combination with one or more biologically or chemically active agents. The skilled medical practitioner can determine the appropriate doses of each agent useful herein, generally reducing the normal dose when RON receptor inhibitor is combined with any of these agents. The RON receptor inhibitor can be administered in the same formulation as the other agent(s) or separate administration of RON receptor inhibitor and the other agent(s) can occur. The other agents are administered in modes, routes, and schedules appropriate for the particular agent.

A typical daily dosage of the RON receptor inhibitor used alone will range from about 0.01 µg/kg to about 1000 mg/kg of body weight per day, depending on the factors mentioned above. Preferably, the daily dosage of the antagonist used alone will be from about 0.1 µg/kg to about 100 mg/kg of body weight per day.

In an alternate embodiment, the present invention provides for a method of treating acute or chronic liver failure comprising administering to the patient a therapeutically effective amount of an inhibitor of phosphatidylinositol 3-kinase ("PI(3)") (for example, wortmannin, LY294002 (Affiniti, Exeter, UK), viridin, viridiol, demethoxyviridin, demethoxyviridiol, and analogs and derivatives thereof) either alone, or in conjunction with a RON receptor inhibitor, e.g., an HGFL truncated protein analog, and/or HGFL or RON receptor blocking antibodies as described above.

Physiologically effective levels of wortmannin range from about 10 to 1000 nM, usually from about 100 to 500 nM, and optimally at about 200 nM. Physiologically effective levels of LY294002 range from about 1 to 500 µM, usually from about 25 to 100 µM, and optimally at about 50 µM. The inhibitors are administered at a dose sufficient to provide for these concentrations in the target tissue.

Other inhibitors of PI(3) kinase include anti-sense reagents that are specific for PI(3) kinase. Of particular interest are anti-sense molecules derived from the human PI(3) kinase sequence, particularly the catalytic p110 subunit, using the publicly available sequence. Alternatively, antibodies, antibody fragments and analogs or other blocking agents are used to bind to the PI(3) kinase in order to reduce the activity.

Representative United States patents that teach the preparation of phosphatidylinositol 3-kinase inhibiting agents include, but are not limited to, U.S. Pat. Nos.: 6,245,754, 5,504,103, 5,480,906, 5,378,725, each of which is herein incorporated by reference.

In another embodiment, the invention relates to a method for the treatment of a patient with a hepatotoxic therapeutic agent effective in the prevention or treatment of a disorder or pathophysiological condition comprising (a) administering to said patient simultaneously or in optional order (1) a biologically effective dose of said therapeutic agent and (2) a preventatively effective amount of a phosphatidylinositol 3-kinase inhibiting agent and (b) monitoring said patient for indication of liver damage and (c) continuing said treatment until the disorder or condition is eliminated or until liver damage is ameliorated. In optional embodiment, the invention comprises in step (a) above, administering to said patient simultaneously or in optional order (1) a biologically effective dose of said therapeutic agent and (2) a preventatively effective amount of a phosphatidylinositol 3-kinase inhibiting agent and (3) a preventatively effective amount of RON receptor inhibiting agent.

In another embodiment, the present invention relates to a method for the prevention of the establishment of liver damage in a patient at risk for developing liver damage comprising administering to said patient a liver damage preventative amount of a phosphatidylinositol 3-kinase inhibiting agent. In a further embodiment, the method includes administering to the patient simultaneously or in optional order a liver damage preventative amount of a RON receptor inhibiting compound. The patient preferably is mammalian, more preferably human.

In the methods of the present invention, the RON receptor inhibiting agent may be administered sequentially or concurrently with the one or more other therapeutic agents. Therapeutic agents contemplated include chemotherapeutics, amino acids, vitamins, immunoadjuvants, growth factors, proteins with growth factor-like activities, such as cytokines or cytokine antagonists, tissue plasminogen activator, antioxidants, nitric oxide donors and compounds capable of inducing nitric oxide generation or other therapeutics.

In another embodiment, the RON receptor inhibiting agent or antagonist may be administered in a composition further comprising an anti-oxidant selected from the group consisting of one or more antioxidants such as methionine, choline, N-acetylcysteine, vitamins (e.g., B complex, vitamin K vitamin E, vitamin A, vitamin C and their derivatives), gluthathione, cysteine, and 2-mercaptoethanol.

In another embodiment, the RON receptor inhibitor may be combined with a vasodilator such as nifedipine, felodipine, verapamil, debrisoquine, clonidine, doxazosin, pazosin, labetalol, irbesartan, lydrallazine, minoxidil, amladipine and nitroglycerine.

In one preferred embodiment, a composition containing the RON receptor inhibitor is administered to a subject mammal alone according to the present invention, or combined with other therapies effective in the prevention or treatment of liver damage wherein the composition further comprises one or more growth factors.

Also included in the invention are "polypeptide growth factors," which possess one or more of the biological functions or activities of the growth factors described herein. Alternatively, polypeptide growth factors useful in the invention can consist of active fragments of the factors. By "active fragment," as used herein in reference to polypeptide growth factors, is meant any portion of a polypeptide that is capable of invoking the same activity as the full-length polypeptide. The active fragment will produce at least 40%, preferably at least 50%, more preferably at least 70%, and most preferably at least 90% (including up to 100%) of the activity of the full-length polypeptide. The activity of any given fragment can be readily determined in any number of ways. For example, a fragment of bFGF that, when administered according to the methods of the invention described herein, is shown to produce performance in functional tests that is comparable to the performance that is produced by administration of the full-length bFGF polypeptide, would be an "active fragment" of bFGF. It is well within the abilities of skilled artisans to determine whether a polypeptide growth factor, regardless of size, retains the functional activity of a full length, wild type polypeptide growth factor.

In another embodiment, the additional therapeutic agent is a nitric oxide (NO) stimulator, a nitric oxide synthase substrate, or a combination thereof. The use of NO donors is known for decreasing blood pressure in the treatment of angina, ischemic diseases, congestive heart failure, impotence in males, hypertension, arteriosclerosis, cerebral vasospasm, and coronary vasospasm (U.S. Pat. Nos. 4,954,526; 5,278,192, incorporated herein by reference in their entirety).

NO therapy is generally achieved by administering drugs, such as nitroglycerine, that donate NO once inside the cell. The rest of the molecule (or NO degradation products) may be metabolically active, thus further complicating the problem of delineating the specific effect of NO on hypertension.

It is known that some NO donors exhibit varying degrees of tolerance that may necessitate intermittent administration of such compounds. For this reason, it may be beneficial to employ organic nitrites that induce less tolerance. Alternatively, it may be preferable to co-administer other agents that help to alleviate the tolerance problem, such as sulfhydryl donors, or to employ agents that stimulate NOS production in vivo, or serve as a substrate for NOS. Such agents include those that stimulate NOS, and those that inhibit the catabolism of NO or feedback inhibition of NOS.

In a further embodiment of the invention, the present invention provides for a method for preventing hepatobiliary damage in a subject due to exposure to a hepatotoxic agent. Such method comprises administering to a subject in need of such treatment a therapeutically effective amount of a composition comprising a RON receptor tyrosine kinase inhibitor wherein the RON receptor inhibitor effectively ameliorates liver damage due to exposure to the hepatotoxic agent. In an additional embodiment, the hepatotoxic agent is one or more of anesthetics, neuropsychotropics, anticonvulsants, analgesics, hormones, antimicrobials, cardiovascular drugs, immunosuppressives, radiation, and antineoplastics. In a preferred embodiment, the administration of RON receptor inhibitor is initiated within 24 hours after exposure to the one or more hepatotoxic agents.

In a further embodiment of the invention, there are provided articles of manufacture and kits containing materials and compositions for inhibiting the RON receptor useful for the prevention and treatment of liver damage or detecting.

The article of manufacture comprises a container with a label. Suitable containers include, for example, bottles, vials, and test tubes. The containers may be formed from a variety of materials such as glass or plastic. The container holds a composition that is effective for the prevention and treatment of liver damage or for detecting or purifying RON receptor. The active agent in the composition is generally a RON receptor antagonist and preferably, comprises Fab fragments of monoclonal antibodies specific for the RON receptor.

The kit of the invention comprises the container described above and a second container comprising a buffer. It may further include other materials desirable from a commercial and user standpoint, including other buffers, diluents, filters, needles, syringes, and package inserts with instructions for use.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,547,932; 5,583,020; 5,591,721; 5,556,948; 5,580,575; and 5,595,756, each of which is herein incorporated by reference.

The RON receptor inhibitors of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For HGFL antagonists, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The present invention also includes pharmaceutical compositions and formulations that include the RON receptor inhibitors of the invention. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

A "pharmaceutical carrier" or "excipient" is a pharmaceutically acceptable solvent, suspending agent or any other pharmacologically inert vehicle for delivering one or more RON receptor inhibitors to an animal. The excipient may be liquid or solid and is selected, with the planned manner of administration in mind, so as to provide for the desired bulk, consistency, etc., when combined with a RON receptor inhibitor and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulfate, etc.).

Pharmaceutically acceptable organic or inorganic excipient suitable for non-parenteral administration that do not deleteriously react with RON receptor inhibitors can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of RON receptor inhibitors may include sterile and non-sterile aqueous solutions, non-aqueous solutions in common solvents such as alcohols, or solutions of the RON receptor inhibitors in liquid or solid oil bases. The solutions may also contain buffers, diluents and other suitable additives. Pharmaceutically acceptable organic or inorganic excipients suitable for non-parenteral administration that do not deleteriously react with RON receptor inhibitors can be used.

Suitable pharmaceutically acceptable excipients include, but are not limited to, water, salt solutions, alcohol, polyethylene glycols, gelatin, lactose, amylose, magnesium stearate, talc, silicic acid, viscous The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the RON receptor inhibitor(s) of the formulation. Aqueous suspensions may contain substances that increase the viscosity of the suspension including, for example, sodium carboxymethylcellulose, sorbitol and/or dextran. The suspension may also contain stabilizers.

Certain embodiments of the invention provide pharmaceutical compositions containing (a) one or more RON receptor inhibitors and (b) one or more other chemotherapeutic agents that function by a non-RON receptor mechanism. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-RON receptor chemotherapeutic agents are also within the scope of this invention. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual HGFL antagonists, and can generally be estimated based on $EC_{50}$ found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The invention is further illustrated in the following examples, which are not intended to be in any way limiting to the scope of the invention as claimed.

EXAMPLES

Example 1

Generation of Truncated HGFL Analogs

The production and characterization of various truncated HGFL proteins was as previously described (Waltz, S. E. et al. (1997), J. Biol. Chem. 272:30526–30537; and Wang, M. H. (1997) J. Biol. Chem. 272:16999–17004). Truncated forms of HGFL lacking the $2^{nd}$ (ΔK2), $3^{rd}$ (ΔK3) or $4^{th}$ (ΔK4) kringle domains, as well as the isolated HGFL β chain, have diminished biological function, yet have near wild-type levels of RON receptor binding activity.

To delineate the functional protein domains necessary for the biological activity of hepatocyte growth factor-like protein (HGFL), we created various site-directed and deletion mutated cDNAs coding for this protein. Wild-type and mutated versions of HGFL were produced after transfection of the corresponding cDNAs into tissue culture cells. The biological importance of the domains within HGFL was then examined by addition of recombinant wild-type or mutant forms of HGFL to assays aimed at elucidating regions involved in the stimulation of DNA synthesis, the induction of shape changes in macrophages, and the ability to stimulate cell scattering. Mutant proteins lacking the serine protease-like domain (light chain) were not biologically active in any of the assays tested and could not compete with wild-type HGFL in cell scattering experiments. These data, in addition to direct enzyme-linked immunosorbent assay analyses, suggest that the light chain may play an important role in the interaction of HGFL with its receptor, Ron. Elimination of the proposed protease cleavage site between the heavy and light chains (by mutation of Arg-483 to Glu) produced a protein with activity comparable to wild-type HGFL. Further studies with this mutated protein uncovered an additional proteolytic cleavage site that produces biologically active protein. Deletion of the various kringle domains or the amino-terminal hairpin loop had various effects in the multiple assays. These data suggest that the heavy chain may play a pivotal role in determining the functional aspects of HGFL.

Generation of Mutants of the Wild-type Human HGFL cDNA. All mutants were generated using the pAlter1 mutagenesis kit (Promega, Madison, Wis.) with the appropriate mutagenic oligonucleotide listed in Table I and a wild-type human HGFL cDNA cloned into pAlter1. The wild-type HGFL cDNA is the cDNA presented in Han et al. (Han, S., Stuart, L. A., and Degen, S. J. F. (1991) Biochemistry 30, 9768–9780), with the sequence from exon 1 included at its 5' end. Mutants were identified by polymerase chain reaction and sequence analysis (ΔK1, ΔK2, ΔK3, ΔK4, ΔK1K2, and ΔPAP) or by sequence analysis alone (Glu, Xa, IIa, ΔL, and K1K2). All mutants were cloned into the EcoRI site of the eukaryotic expression vector pcDNA3 (Invitrogen, Carlsbad, Calif.) in the proper orientation for expression after transient and stable transfections. One additional mutation was generated at nucleotide 48 in the signal sequence. Our original cDNA had an A at this position, whereas a G was present in the gene. This resulted in a tyrosine at amino acid 13 in the cDNA and a cysteine at this position in the gene. Because we were not sure what this difference would have on the expression of recombinant HGFL, we performed site-directed mutagenesis using the Chameleon kit (Stratagene, La Jolla, Calif.) and oligonucleotide 48G. The appropriate substitution was identified by DNA sequence analysis.

transferred by electrophoresis to polyvinylidene fluoride membranes in 25 mM Tris-HCl, 192 mM glycine, and 20% methanol at 4° C. for 4 h at 250 mA. The membrane was probed with a polyclonal anti-HGFL rabbit antibody. The polyclonal antibody extensively used for HGFL detection was raised in rabbits against a fusion protein of beta-galactosidase and a 960-base pair cDNA fragment coding for 321 amino acids of human HGFL (including part of the second kringle to the carboxyl terminus of the protein, which included part of the serine protease-like domain).

Mitogenic Assays. CMT-93 cells were seeded in triplicate in 100 ml of complete medium at a concentration of $5 \times 10^3$ cells/well in a 96-well tissue culture plate. Two days later, the medium was aspirated and 200 ml of medium containing 0.5% serum was added. After 48 h, recombinant HGFL protein (a concentration of 200–400 ng/ml was found to be optimal) was added. Two days after recombinant protein addition, 10 ml of 5-bromo-29-deoxyuridine (BrdUrd) was added for 16 h. The amount of BrdUrd incorporation was determined using an ELISA-based BrdUrd labeling and detection kit from Boehringer Mannheim according to the manufacturer's instructions.

Receptor Binding Assays. 293/Ron cells were grown to approximately 70% confluence in 60-mm tissue culture plates in complete medium. The cells were washed three times with ice-cold PBS, and recombinant protein (or appropriate controls) was added for 1 h at 37° C. Detachment from the tissue culture plates was accomplished in 2 ml of Versene in PBS. The cells were rinsed twice in ice-cold PBS, followed by resuspension in a solution of PBS containing 1% bovine serum albumin and a 1:1 mixture of antibodies

TABLE I

Oligonucleotides used in creating wild-type and mutant forms of HGFL

| Mutant | HGFL sequence | | Nucleotides |
|---|---|---|---|
| ΔPAP | ATGTGGCAGATGCTGAAGAGCAACTGCTGCCATGGACTCA | (SEQ ID NO:5) | 146–165, 235–254 |
| ΔK1 | AGAAAGACTACGTACGGACCCGGGAGGCCGCGTGTGTCTG | (SEQ ID NO:6) | 308–327, 559–578 |
| ΔK2 | GCTGCGGCATCAAATCCTGCGGGTCCGAGGCACAGCCCCG | (SEQ ID NO:7) | 539–558, 805–824 |
| ΔK | AAGAGGCCACAACTGTCAGCACAGACGACGTGCGGCCCCA | (SEQ ID NO:8) | 3827–846, 1084–1103 |
| ΔK4 | ACGACGTGCGGCCCCAGGACGCTGATGACCAGCCGCCATC | (SEQ ID NO:9) | 1088–1107, 1345–1364 |
| ΔK1K2 | AGAAAGACTACGTACGGACCGGGTCCGAGGCACAGCCCCG | (SEQ ID NO:10) | 308–327, 805–824 |
| ΔL | CGTTCCAAGCTGCGCtagGTGGTTGGGGGCCAT | (SEQ ID NO:11) | 1435–1464[a] |
| K1K2 | GGGTCCGAGGCACAGtagCCCCGCCAAGAGGCC | (SEQ ID NO:12) | 805–834[a] |
| Glu | CGGCGTTCCAAGCTGgagGTGGTTGGGGGCCAT | (SEQ ID NO:13) | 1432–1464[b] |
| Xa | CTGGATCAGCGGCGTatcgaaggtCGCGTGGTTGGGGGC | (SEQ ID NO:14) | 1423–1461[b] |
| IIa | CTGGATCAGCGGCGTctggttccgCGCGTGGTTGGGGGC | (SEQ ID NO:15) | 1423–1461[b] |
| 48G | CCAGGGACCCCTAAGcATTGAGTCAGAAGC | (SEQ ID NO:16) | 24–53 |

[a]Inserted stop codon (lowercase).
[b]Nucleotide substitutions to replace activation site with Glu for Arg-483, thrombin (Leu-Val-Pro-Arg) (SEQ ID NO:17), or factor Xa (Ile-Glu-Gly-Arg) (SEQ ID NO:18) recognition sequence (lowercase).

Detection and Quantification of Wild-type and Mutant HGFL Proteins. For analysis of secreted recombinant protein, cell culture supernatants were resolved by SDS-polyacrylamide gel electrophoresis on 10% gels under denaturing conditions. After electrophoresis, the proteins were directed against HGFL and an anti-rabbit-fluorescein conjugate. After a 30-min incubation period on ice, the cells were washed twice with ice-cold PBS followed by fixation in PBS containing 1% paraformaldehyde. The cells were then analyzed by measuring fluorescence intensity on a Becton Dickinson FACScan flow cytometer. Results are expressed as the mean channel fluorescence of 10,000 cells using logarithmic amplification.

Detection of Interaction of Purified Ron with Recombinant Variants of HGFL by Direct ELISA. The Ron protein was purified by an anti-Ron affinity column as described previously (Wang, M. -H., Montero-Julian, F. A., Dauny, I., and Leonard, E. J. (1996) Oncogene 13, 2167–2175). To study the interaction of Ron with multiple HGFL recombinant proteins, the Ron receptor was purified, placed in a 96-well ELISA plate at 50 ng/well, and incubated overnight at 4° C. Supernatants were collected from cells transfected with different HGFL variant cDNAs, and equal amounts of HGFL recombinant proteins were added to the wells and incubated at 37° C. for 90 min. To measure the amount of captured recombinant protein, an antibody against HGFL was added (Wang, M. -H., Montero-Julian, F. A., Dauny, I., and Leonard, E. J. (1996) Oncogene 13, 2167–2175). For detection analyses, an anti-rabbit IgG antibody conjugated with horseradish peroxidase (Boehringer Mannheim) was applied to the wells. The reaction was developed with substrate, and the A405 was measured in an ELISA plate reader. Each sample was tested in duplicate. The single-chain form of HGFL was utilized initially for these experiments. However, it became apparent that processed preparations were needed for full activity. Thus, the wild-type (WT) HGFL contains significant amounts of proteolytically cleaved protein.

Results

Generation and Expression of Recombinant HGFL Protein. In an effort to identify important structural domains involved in the function of HGFL, a panel of mutated cDNAs of HGFL were constructed. Eight deletion mutants and four site-directed mutants of HGFL were created by oligonucleotide-directed mutagenesis. The deletion mutants were created by deletion of the cDNA sequence corresponding to the HGFL domain of interest ($\Delta$PAP, $\Delta$K1, $\Delta$K2, $\Delta$K3, $\Delta$K4, $\Delta$K1K2, or sequence following kringle 2 as in K1K2). Deletion of the light chain of HGFL ($\Delta$L) was accomplished by creating a stop codon (TAG) after amino acid 483, immediately preceding the activation site. To study the effect of proteolytic cleavage as it relates to HGFL function, a mutation that disrupts the putative cleavage site was also created with the substitution of Glu for Arg-483 at the activation site (Glu). Furthermore, two mutations were created in which an engineered processing site for factor Xa (Xa) or thrombin (IIa) was created at the putative activation site of HGFL. The Xa processing site changed amino acids Ser-480, Lys-481, Gly-482 to Ile-480, Glu-481, and Gly-482, whereas the IIa site was created by changing these amino acids to Leu, Val, and Pro, respectively.

All of the cDNAs for the corresponding proteins were cloned into the eukaryotic expression vector pcDNA3 and transfected either stably into CHO cells or transiently into 293 cells. Serum-free culture medium from the transfected cells was used as a source of recombinant HGFL. A majority of the protein products appeared to consist of the single-chain form of HGFL. In culture medium from untransfected cells, as well as both stable and transient transfections with wild-type and mutant forms of HGFL, variable nonspecific background was also seen.

Mitogenic Effects of Various HGFL Mutant Proteins on CMT-93 Cells. The ability of wild-type and mutated versions of HGFL was examined for their capability to stimulate cell growth. Although the function of Ron in this context is not known, Ron may be involved in the proliferative capacity of the intestinal epithelia, a cell layer that is constantly being turned over. Equal concentrations of wild-type and HGFL recombinants were applied to the rectal carcinoma cell line, CMT-93. Mitogenic activity was then determined based on the amount of nucleotide analogue, BrdUrd, incorporated. The amount of background incorporation of BrdUrd as a result of medium from untransfected cultures was set to 1, and the -fold stimulation of each of the recombinant proteins was calculated. Wild-type human HGFL (WT) along with the putative unprocessed forms of HGFL (Glu, IIa, and Xa) appeared to stimulate cell growth by 2-fold. The K1K2 mutant also stimulated growth in this range, whereas deletion of the light chain ($\Delta$L) or deletion of kringle 2, kringle 4, or both kringles 1 and 2 abrogated the mitogenic effects.

Alternative Proteolytic Cleavage Site for Activation of HGFL. Conversion of HGFL to its active heterodimeric form is thought to occur by proteolytic cleavage involving specific serine-proteases at an Arg-Val bond between amino acids 483 and 484. Abolishment of the Arg site in HGFL, as in the Glu mutation, however, results in a protein with functional activities comparable to the wild-type protein as judged in mitogenic assays.

Previous studies have suggested that the addition of soybean trypsin inhibitor ("STI") to assays of HGFL function may enhance activity by inhibiting nonspecific degradation. Addition of this protease inhibitor appeared to cause enhanced digestion at the putative Arg483 site in the wild-type protein producing more of the 53-kDa product under prolonged digestion conditions. Digestions containing STI and kallikrein with the Glu mutant, however, appeared to partially inhibit cleavage at the putative alternative processing site. These data suggest that STI may be acting to cause selective cleavage by kallikrein at the Arg-483 site, whereas kallikrein alone appears to act at either site.

Binding of HGFL and Mutant Forms to 293/Ron Cells. For HGFL, deletion of the light chain ($\Delta$L) causes not only loss of biological activity but possibly loss of receptor binding. To further investigate receptor binding properties of HGFL and various mutants at the concentrations used in this study, flow cytometry and receptor binding competition experiments were performed. Competition experiments testing the ability of mutant forms of HGFL to compete for wild-type binding and function in cell scattering assays were performed. As determined previously, three mutants (namely $\Delta$L, $\Delta$K2, and $\Delta$K3) were unable to produce a cell scattering phenotype. Lack of scattering function may be either a direct result of mutation of a region important for cell scattering or an indirect result of creating a mutant that loses the ability to bind to its receptor.

To directly access the quantitative ability of the recombinant HGFL proteins to associate with Ron, a quantitative ELISA assay was developed. For these analyses, the Ron receptor was affinity purified and coated on the bottoms of a 96-well ELISA plate. Subsequently, equal amounts of recombinant wild-type and mutant HGFL proteins were added. After incubation, the amount of recombinant protein that remained bound to the Ron receptor was determined. In these analyses, it became apparent that the single-chain unprocessed form of HGFL did not associate with the purified receptor. However, when processed HGFL was added in the direct ELISA experiments, binding to Ron was detected.

Example 2

Effect of Endotoxin/Galactosamine in Mice Lacking the Tyrosine Kinase Domain of the RON Receptor Mice injected intraperitoneally with various doses of endotoxin and galactosamine were sacrificed at 9 hours, and serum and liver tissue was obtained for routine analysis. Serum alanine aminotransferase levels and liver histology were remarkably normal in experimental TK$^{-/-}$ mice compared to control mice. In addition, indices of apoptosis, including in situ TUNEL assay and DNA ladder analysis by gel electrophoresis, were dramatically diminished in experimental animals. Nitrotyrosine deposition, a marker of nitric oxide generation, was determined by immunohistochemistry of liver tissue. Elevation of nitrotyrosine deposition was noted in TK$^{-/-}$ mice compared to controls in both mock and LPS/GalN-treated animals.

The β chain of HGFL (also known as MSP β chain) has been shown to bind to the Ron receptor, yet not cause any biological effects following receptor binding. This compound, then, could serve as a Ron receptor antagonist in vivo. Injection of wild type mice with the β chain of HGFL just prior to, and concurrent with, administration of hepatotoxic doses of endotoxin and galactosamine, leads to a protected liver injury phenotype, similar to that seen in mice with the targeted deletion of the cytoplasmic tyrosine kinase domain of the Ron receptor.

Sex- and age- matched wild type littermate mice were injected intravenously with either 30 μg of human recombinant HGFL β chain or carrier, 30 minutes prior to the intraperitoneal injection of 3.3 μg of lipopolysaccharide (LPS) and 25 mg of galactosamine (GalN). A second identical dose of either HGFL β chain or carrier was injected at 3 hours post LPS/GalN injection. At 6 hours post-LPS/GalN injection, the liver was obtained and assessed both grossly and by routine (hematoxylin and eosin) histology for degree of necrosis. Statistical significance was determined by $X^2$ analysis; results are the sum of two individual experiments.

| Pre-LPS/GalN treatment with | | |
|---|---|---|
| Gross liver | saline | HGFL β chain |
| normal | 9 | 10 |
| black | 5 | 0 |

$p = 0.024$

| Histology (H&E) | | |
|---|---|---|
| >10% necrosis | saline | HGFL β chain |
| Negative | 8 | 9 |
| Positive | 6 | 1 |

$p = 0.038$

| Histology (H&E) | | |
|---|---|---|
| >50% necrosis | saline | HGFL β chain |
| Negative | 8 | 10 |
| Positive | 6 | 0 |

$p = 0.011$

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for the treatment of hepatobiliary damage in a subject comprising (a) identifying a subject in need of treatment for hepatobiliary damage; (b) administering to the subject a therapeutically effective amount of a composition comprising a RON receptor tyrosine kinase inhibitor wherein the RON receptor tyrosine kinase inhibitor is an HGFL protein antagonist and wherein the HGFL protein antagonist comprises a polypeptide sequence of at least the C-terminal serine protease-like domain of an MSP beta-chain protein (SEQ ID NO:2); wherein the polypeptide comprises at least 9 contiguous amino acids of SEQ ID NO:2 and is less than 100 amino acids in length; wherein the polypeptide sequence is lacking at least one kringle region selected from the group comprising the $2^{nd}$ (ΔK2), $3^{rd}$ (ΔK3) or $4^{th}$ (ΔK4) kringle domains; and wherein the polypeptide is capable of binding the RON receptor and preventing activation of the RON receptor by HGFL; and (c) continuing the administration of the composition for a time sufficient to treat hepatobiliary damage in the subject.

2. The method according to claim 1, wherein the polypeptide is lacking at least one kringle region selected from the group comprising the $2^{nd}$ (ΔK2) and $3^{rd}$ (ΔK3) kringle domains.

3. The method according to claim 2, wherein the polypeptide is lacking both the $2^{nd}$ (ΔK2) and $3^{rd}$ (ΔK3) kringle domains.

4. The method according to claim 3, wherein the HGFL protein antagonist is a polypeptide comprising an amino acid sequence at least 20 amino acids in length that includes at least 9 contiguous amino acids of a polypeptide sequence shown in SEQ ID NO:2.

5. The method according to claim 2, wherein the composition further comprises at least one additional therapeutic agent.

6. The method according to claim 5, wherein the composition further comprises at least one additional component selected from the group consisting of pharmaceutically acceptable carriers, adjuvants, emulsifiers, solubilizers, and stabilizers.

7. The method according to claim 5, wherein the at least one additional therapeutic agent is selected from the group consisting of chemotherapeutics, amino acids, antisense molecules, vitamins, immunoadjuvants, growth factors, proteins with growth factor-like activities, such as cytokines or cytokine antagonists, tissue plasminogen activator, antioxidants, nitric oxide donors and compounds capable of inducing nitric oxide generation or other therapeutics.

8. The method according to claim 7, wherein the at least one additional therapeutic agent is an antioxidant selected from the group consisting of an agent such as methionine, choline, N-acetylcysteine, vitamins, glutathione, cysteine, and 2-mercaptoethanol.

9. The method according to claim 5, wherein the at least one additional therapeutic agent is an inhibitor of phosphatidylinositol 3-kinase.

10. The method according to claim 9, wherein the inhibitor of phosphatidylinositol 3-kinase is selected from the group consisting of wortmannin, LY294002 (Affiniti, Exeter, UK), viridin, viridiol, demethoxyviridin, demethoxyviridiol, and analogs and derivatives thereof.

11. The method according to claim 2, wherein the hepatobiliary system injury is acute liver failure.

12. The method according to claim 2, wherein the hepatobiliary system injury is chronic liver failure.

13. The method according to claim 2, wherein the RON receptor inhibitor is a pharmaceutically acceptable salt.

14. The method according to claim 13, wherein the RON receptor inhibitor is a prodrug.

15. The method according to claim 13, wherein the composition is administered orally, intravenously, transcutaneously or transdermally.

16. The method according to claim 7, wherein the at least one additional therapeutic agent is a therapeutically effective amount of a nitric oxide stimulator.

17. The method according to claim 16, wherein the nitric oxide stimulator is one or more agents selected from the group consisting of nitric oxide donors, NO synthase (NOS) stimulators, and NO catabolism inhibitors.

18. The method according to claim 16, wherein the nitric oxide stimulator is a nitric oxide donor selected from the group consisting of nitroglycerin, amyl nitrate, nitroprusside, isosorbide dinitrate, erythityl dinitrate, and pentaerythritol tetranitrate.

19. The method according to claim 2, wherein the RON receptor inhibitor is capable of binding to the RON receptor and thereby inhibits receptor homo or heterodimerization with another protein receptor tyrosine kinase.

20. The method according to claim 1, wherein said method further comprises during the administration step, the additional steps of (d) monitoring the subject for indications of hepatobiliary condition, and optionally, (e) adjusting the time and amount of administration of the composition as necessary based on the indications.

* * * * *

UNITED STATES PATENT AND TRADEMARK OFFICE
CERTIFICATE OF CORRECTION

| | | |
|---|---|---|
| PATENT NO. | : 7,235,523 B2 | |
| APPLICATION NO. | : 10/123036 | |
| DATED | : June 26, 2007 | |
| INVENTOR(S) | : Waltz et al. | |

It is certified that error appears in the above-identified patent and that said Letters Patent is hereby corrected as shown below:

Column 1, Line 9, please delete "in part with".

Column 1, Line 12, please change "may have" to "has".

Signed and Sealed this

Sixth Day of October, 2009

David J. Kappos
*Director of the United States Patent and Trademark Office*

SEQUENCE LISTING

```
<160> NUMBER OF SEQ ID NOS: 16

<210> SEQ ID NO 1
<211> LENGTH: 2216
<212> TYPE: DNA
<213> ORGANISM: Homo sapiens

<400> SEQUENCE: 1 atgggggtggc tcccactcct gctgcttctg actcaatact tagggggtccc tgggcagcgc      60 tcgccattga atgacttcca agtgctccgg ggcacagagc tacagcacct gctacatgcg     120
gtggtgcccg ggccttggca ggaggatgtg gcagatgctg aagagtgtgc tggtcgctgt     180
gggcccttaa tggactgccg ggccttccac tacaacgtga gcagccatgg ttgccaactg     240
ctgccatgga ctcaacactc gccccacacg aggctgcggc gttctggggcg ctgtgacctc     300 ttccagaaga aagactacgt acggacctgc atcatgaaca atggggttgg gtaccggggc     360
accatggcca cgaccgtggg tggcctgccc tgccaggctt ggagccacaa gttcccgaat     420
gatcacaagt acacgcccac tctccggaat ggcctggaag agaacttctg ccgtaaccct     480
```

-continued

```
gatggcgacc ccggaggtcc ttggtgctac acaacagacc ctgctgtgcg cttccagagc    540
tgcggcatca atcctgccg ggaggccgcg tgtgtctggt gcaatggcga ggaataccgc    600
ggcgcggtag accgcacgga gtcagggcgc gagtgccagc gctgggatct tcagcacccg    660
caccagcacc ccttcgagcc gggcaagttc ctcgaccaag gtctggacga caactattgc    720
cggaatcctg acggctccga gcggccatgg tgctacacta cggatccgca gatcgagcga    780
gagttctgtg acctcccccg ctgcgggtcc gaggcacagc ccgccaaga ggccacaact    840
gtcagctgct ccgcgggaa gggtgagggc taccggggca cagccaatac caccactgcg    900
ggcgtacctt gccagcgttg ggacgcgcaa atccctcatc agcaccgatt tacgccagaa    960
aaatacgcgt gcaaagacct tcgggagaac ttctgccgga accccgacgg ctcagaggcg   1020
ccctggtgct tcacactgcg gcccggcatg cgcgcggcct tttgctacca gatccggcgt   1080
tgtacagacg acgtgcggcc ccaggactgc taccacggcg caggggagca gtaccgcggc   1140
acggtcagca agacccgcaa gggtgtccag tgccagcgct ggtccgctga cgccgcac    1200
aagccgcagt tcacgtttac ctccgaaccc atgcacaac tggaggagaa cttctgccgg    1260
aacccagatg gggatagcca tgggccctgg tgctacacga tggacccaag gaccccattc    1320
gactactgtg ccctgcgacg ctgcgctgat gaccagccgc catcaatcct ggaccccca    1380
gaccaggtgc agtttgagaa gtgtggcaag agggtggatc ggctggatca gcggcgttcc    1440
aagctgcgcg tggttggggg ccatccgggc aactcaccct ggacagtcag cttgcggaat    1500
cggcagggcc agcatttctg cggggggtct ctagtgaagg agcagtggat actgactgcc    1560
cggcagtgct tctcctcctg ccatatgcct ctcacgggct atgaggtatg gttgggcacc    1620
ctgttccaga acccacagca tggagagcca agcctacagc gggtcccagt agccaagatg    1680
gtgtgtgggc cctcaggctc ccagcttgtc ctgctcaagc tggagagatc tgtgaccctg    1740
aaccagcgcg tggccctgat ctgcctgccc cctgaatggt atgtggtgcc tccagggacc    1800
aagtgtgaga ttgcaggctg gggtgagacc aaaggtacgg gtaatgacac agtcctaaat    1860
gtggccttgc tgaatgtcat ctccaaccag gagtgtaaca tcaagcaccg aggacgtgtg    1920
cgtgagagtg agatgtgcac tgagggactg ttggcccctg tggggcctg tgagggtgac    1980
tacggggggcc cacttgcctg ctttacccac aactgctggg tcctggaagg aattataatc    2040
cccaaccgag tatgcgcaag gtcccgctgg ccagctgtct tcacgcgtgt ctctgtgttt    2100
gtggactgga ttcacaaggt catgagactg ggttaggccc agccttgatg ccatatgcct    2160
tggggaggac aaaacttctt gtcagacata aagccatgtt tcctctttat gcctgt       2216
```

<210> SEQ ID NO 2
<211> LENGTH: 711
<212> TYPE: PRT
<213> ORGANISM: Homo sapiens

<400> SEQUENCE: 2

```
Met Gly Trp Leu Pro Leu Leu Leu Leu Thr Gln Tyr Leu Gly Val
1               5                   10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
        50                  55                  60
```

```
Asp Cys Arg Ala Phe His Tyr Asn Val Ser Ser His Gly Cys Gln Leu
 65                  70                  75                  80

Leu Pro Trp Thr Gln His Ser Pro His Thr Arg Leu Arg Arg Ser Gly
                 85                  90                  95

Arg Cys Asp Leu Phe Gln Lys Lys Asp Tyr Val Arg Thr Cys Ile Met
                100                 105                 110

Asn Asn Gly Val Gly Tyr Arg Gly Thr Met Ala Thr Thr Val Gly Gly
                115                 120                 125

Leu Pro Cys Gln Ala Trp Ser His Lys Phe Pro Asn Asp His Lys Tyr
130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
                180                 185                 190

Trp Cys Asn Gly Glu Glu Tyr Arg Gly Ala Val Asp Arg Thr Glu Ser
                195                 200                 205

Gly Arg Glu Cys Gln Arg Trp Asp Leu Gln His Pro His Gln His Pro
210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
                260                 265                 270

Gln Pro Arg Gln Glu Ala Thr Thr Val Ser Cys Phe Arg Gly Lys Gly
                275                 280                 285

Glu Gly Tyr Arg Gly Thr Ala Asn Thr Thr Thr Ala Gly Val Pro Cys
                290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
                340                 345                 350

Ala Phe Cys Tyr Gln Ile Arg Arg Cys Thr Asp Asp Val Arg Pro Gln
                355                 360                 365

Asp Cys Tyr His Gly Ala Gly Glu Gln Tyr Arg Gly Thr Val Ser Lys
                370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
                420                 425                 430

Thr Met Asp Pro Arg Thr Pro Phe Asp Tyr Cys Ala Leu Arg Arg Cys
                435                 440                 445

Ala Asp Asp Gln Pro Pro Ser Ile Leu Asp Pro Pro Asp Gln Val Gln
450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
```

```
                      485              490              495
Ser Leu Arg Asn Arg Gln Gly Gln His Phe Cys Gly Gly Ser Leu Val
                500              505              510
Lys Glu Gln Trp Ile Leu Thr Ala Arg Gln Cys Phe Ser Ser Cys His
            515              520              525
Met Pro Leu Thr Gly Tyr Glu Val Trp Leu Gly Thr Leu Phe Gln Asn
        530              535              540
Pro Gln His Gly Glu Pro Ser Leu Gln Arg Val Pro Val Ala Lys Met
545              550              555              560
Val Cys Gly Pro Ser Gly Ser Gln Leu Val Leu Lys Leu Glu Arg
                565              570              575
Ser Val Thr Leu Asn Gln Arg Val Ala Leu Ile Cys Leu Pro Pro Glu
            580              585              590
Trp Tyr Val Pro Pro Gly Thr Lys Cys Glu Ile Ala Gly Trp Gly
        595              600              605
Glu Thr Lys Gly Thr Gly Asn Asp Thr Val Leu Asn Val Ala Leu Leu
    610              615              620
Asn Val Ile Ser Asn Gln Glu Cys Asn Ile Lys His Arg Gly Arg Val
625              630              635              640
Arg Glu Ser Glu Met Cys Thr Glu Gly Leu Leu Ala Pro Val Gly Ala
                645              650              655
Cys Glu Gly Asp Tyr Gly Gly Pro Leu Ala Cys Phe Thr His Asn Cys
            660              665              670
Trp Val Leu Glu Gly Ile Ile Ile Pro Asn Arg Val Cys Ala Arg Ser
        675              680              685
Arg Trp Pro Ala Val Phe Thr Arg Val Ser Val Phe Val Asp Trp Ile
690              695              700
His Lys Val Met Arg Leu Gly
705              710

<210> SEQ ID NO 3
<211> LENGTH: 4541
<212> TYPE: DNA
<213> ORGANISM: Homo sapiens

<400> SEQUENCE: 3
ggatcctcta gggtcccagc tcgcctcgat ggagctcctc ccgccgctgc ctcagtcctt      60
cctgttgctg ctgctgttgc ctgccaagcc cgcggcgggc gaggactgga agtgcccgcg     120
caccccctac gcggcctctc gcgactttga cgtgaagtac gtggtgccca gcttctccgc     180
cggaggcctg gtacaggcca tggtgaccta cgagggcgac agaaatgaga gtgctgtgtt     240
tgtagccata cgcaatcgcc tgcatgtgct tgggcctgac ctgaagtctg tccagagcct     300
ggccacgggc cctgctggag accctggctg ccagacgtgt gcagcctgtg cccaggacc     360 ccacggccct cccggtgaca cagacacaaa ggtgctggtg ctggatcccg cgctgcctgc     420
gctggtcagt tgtggctcca gcctgcaggg ccgctgcttc ctgcatgacc tagagcccca     480
agggacagcc gtgcatctgg cagcgccagc ctgcctcttc tcagcccacc ataaccggcc     540
cgatgactgc cccgactgtg tggccagccc attgggcacc cgtgtaactg tggttgagca     600
aggccaggcc tcctatttct acgtggcatc ctcactggac gcagccgtgg ctggcagctt     660
cagcccacgc tcagtgtcta tcaggcgtct caaggctgac gcctcgggat tcgcaccggg     720
ctttgtggcg ttgtcagtgc tgcccaagca tcttgtctcc tacagtattg aatacgtgca     780
cagcttccac acgggagcct tcgtatactt cctgactgta cagccggcca gcgtgacaga     840
```

-continued

| | |
|---|---|
| tgatcctagt gccctgcaca cacgcctggc acggcttagc gccactgagc cagagttggg | 900 |
| tgactatcgg gagctggtcc tcgactgcag atttgctcca aaacgcaggc gccgggggc | 960 |
| cccagaaggc ggacagccct accctgtgct gcaggtggcc cactccgctc cagtgggtgc | 1020 |
| ccaacttgcc actgagctga gcatcgccga gggccaggaa gtactatttg gggtctttgt | 1080 |
| gactggcaag gatggtggtc ctggcgtggg ccccaactct gtcgtctgtg ccttccccat | 1140 |
| tgacctgctg gacacactaa ttgatgaggg tgtggagcgc tgttgtgaat ccccagtcca | 1200 |
| tccaggcctc cggcgaggcc tcgacttctt ccagtcgccc agttttttgcc ccaacccgcc | 1260 |
| tggcctggaa gccctcagcc ccaacaccag ctgccgccac ttccctctgc tggtcagtag | 1320 |
| cagcttctca cgtgtggacc tattcaatgg gctgttggga ccagtacagg tcactgcatt | 1380 |
| gtatgtgaca cgccttgaca acgtcacagt ggcacacatg ggcacaatgg atgggcgtat | 1440 |
| cctgcaggtg gagctggtca ggtcactaaa ctacttgctg tatgtgtcca acttctcact | 1500 |
| gggtgacagt gggcagcccg tgcagcggga tgtcagtcgt cttggggacc acctactctt | 1560 |
| tgcctctggg gaccaggttt ccaggtacc tatccgaggc cctggctgcc gccacttcct | 1620 |
| gacctgtggg cgttgcctaa gggcatggca tttcatgggc tgtggctggt gtgggaacat | 1680 |
| gtgcggccag cagaaggagt gtcctggctc ctggcaacag gaccactgcc cacctaagct | 1740 |
| tactgagttc cacccccaca gtggacctct aaggggcagt acaaggctga ccctgtgtgg | 1800 |
| ctccaacttc taccttcacc cttctggtct ggtgcctgag ggaacccatc aggtcactgt | 1860 |
| gggccaaagt ccctgccggc cactgccaa ggacagctca aaactcagac cagtgccccg | 1920 |
| gaaagacttt gtagaggagt ttgagtgtga actggagccc ttgggcaccc aggcagtggg | 1980 |
| gcctaccaac gtcagcctca ccgtgactaa catgccaccg ggcaagcact tccgggtaga | 2040 |
| cggcacctcc gtgctgagag gcttctcttt catggagcca gtgctgatag cagtgcaacc | 2100 |
| cctctttggc ccacgggcag gaggcacctg tctcactctt gaaggccaga gtctgtctgt | 2160 |
| aggcaccagc cgggctgtgc tggtcaatgg gactgagtgt ctgctagcac gggtcagtga | 2220 |
| ggggcagctt ttatgtgcca cacccctgg ggccacggtg gccagtgtcc ccttagcct | 2280 |
| gcaggtgggg ggtgcccagg tacctggttc ctggaccttc cagtacagag aagaccctgt | 2340 |
| cgtgctaagc atcagcccca actgtggcta catcaactcc cacatcacca tctgtggcca | 2400 |
| gcatctaact tcagcatggc acttagtgct gtcattccat gacgggctta gggcagtgga | 2460 |
| aagcaggtgt gagaggcagc ttccagagca gcagctgtgc cgccttcctg aatatgtggt | 2520 |
| ccgagacccc cagggatggg tggcagggaa tctgagtgcc cgagggatg gagctgctgg | 2580 |
| ctttacactg cctggctttc gcttcctacc cccacccat ccaccagtg ccaacctagt | 2640 |
| tccactgaag cctgaggagc atgccattaa gtttgagtat attgggctgg gcgctgtggc | 2700 |
| tgactgtgtg ggtatcaacg tgaccgtggg tggtgagagc tgccagcacg agttccgggg | 2760 |
| ggacatggtt gtctgccccc tgcccccatc cctgcagctt ggccaggatg gtgccccatt | 2820 |
| gcaggtctgc gtagatggtg aatgtcatat cctgggtaga gtggtgcggc cagggccaga | 2880 |
| tggggtccca cagagcacgc tccttggtat cctgctgcct ttgctgctgc ttgtggctgc | 2940 |
| actggcgact gcactggtct tcagctactg gtggcggagg aagcagctag ttcttcctcc | 3000 |
| caacctgaat gacctggcat ccctggacca gactgctgga gccacacccc tgcctattct | 3060 |
| gtactcgggc tctgactaca gaagtggcct tgcactccct gccattgatg gtctggattc | 3120 |
| caccacttgt gtccatggag catccttctc cgatagtgaa gatgaatcct gtgtgccact | 3180 |

-continued

```
gctgcggaaa gagtccatcc agctaaggga cctggactct gcgctcttgg ctgaggtcaa    3240
ggatgtgctg attccccatg agcgggtggt cacccacagt gaccgagtca ttggcaaagg    3300
ccactttgga gttgtctacc acggagaata catagaccag gcccagaatc gaatccaatg    3360
tgccatcaag tcactaagtc gcatcacaga gatgcagcag gtggaggcct tcctgcgaga    3420
ggggctgctc atgcgtggcc tgaaccaccc gaatgtgctg gctctcattg gtatcatgtt    3480
gccacctgag ggcctgcccc atgtgctgct gccctatatg tgccacggtg acctgctcca    3540
gttcatccgc tcacctcagc ggaaccccac cgtgaaggac ctcatcagct ttggcctgca    3600
ggtagcccgc ggcatggagt acctggcaga gcagaagttt gtgcacaggg acctggctgc    3660
gcggaactgc atgctggacg agtcattcac agtcaaggtg gctgactttg gtttggcccg    3720
cgacatcctg gacagggagt actatagtgt tcaacagcat cgccacgctc gcctacctgt    3780
gaagtggatg gcgctggaga gcctgcagac ctatagattt accaccaagt ctgatgtgtg    3840
gtcatttggt gtgctgctgt gggaactgct gacacgggt gccccaccat accgccacat    3900
tgacccttt gaccttaccc acttcctggc ccagggtcgg cgcctgcccc agcctgagta    3960
ttgccctgat tctctgtacc aagtgatgca gcaatgctgg gaggcagacc cagcagtgcg    4020
acccaccttc agagtactag tgggggaggt ggagcagata gtgtctgcac tgcttgggga    4080
ccattatgtg cagctgccag caacctacat gaacttgggc cccagcacct cgcatgagat    4140
gaatgtgcgt ccagaacagc cgcagttctc acccatgcca gggaatgtac gccggccccg    4200
gccactctca gagcctcctc ggcccacttg acttagttct tgggctggac ctgcttagct    4260
gccttgagct aaccccaagg ctgcctctgg gccatgccag gccagagcag tggccctcca    4320
ccttgttcct gcccttaac tttcagaggc aataggtaaa tgggcccatt aggtccctca    4380
ctccacagag tgagccagtg agggcagtcc tgcaacatgt atttatggag tgcctgctgt    4440
ggaccctgtc ttctgggcac agtggactca gcagtgacca caccaacact gacccttgaa    4500
ccaataaagg aacaaatgac tattaaagca caaaaaaaaa a                        4541
```

<210> SEQ ID NO 4
<211> LENGTH: 1400
<212> TYPE: PRT
<213> ORGANISM: Homo sapiens

<400> SEQUENCE: 4

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly His His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
```

-continued

```
            130                 135                 140
Leu His Asp Leu Glu Pro Gln Gly Thr Ala Val His Leu Ala Ala Pro
145                 150                 155                 160
Ala Cys Leu Phe Ser Ala His His Asn Arg Pro Asp Asp Cys Pro Asp
                165                 170                 175
Cys Val Ala Ser Pro Leu Gly Thr Arg Val Thr Val Glu Gln Gly
            180                 185                 190
Gln Ala Ser Tyr Phe Tyr Val Ala Ser Ser Leu Asp Ala Ala Val Ala
            195                 200                 205
Gly Ser Phe Ser Pro Arg Ser Val Ser Ile Arg Arg Leu Lys Ala Asp
210                 215                 220
Ala Ser Gly Phe Ala Pro Gly Phe Val Ala Leu Ser Val Leu Pro Lys
225                 230                 235                 240
His Leu Val Ser Tyr Ser Ile Glu Tyr Val His Ser Phe His Thr Gly
                245                 250                 255
Ala Phe Val Tyr Phe Leu Thr Val Gln Pro Ala Ser Val Thr Asp Asp
            260                 265                 270
Pro Ser Ala Leu His Thr Arg Leu Ala Arg Leu Ser Ala Thr Glu Pro
            275                 280                 285
Glu Leu Gly Asp Tyr Arg Glu Leu Val Leu Asp Cys Arg Phe Ala Pro
290                 295                 300
Lys Arg Arg Arg Arg Gly Ala Pro Glu Gly Gly Gln Pro Tyr Pro Val
305                 310                 315                 320
Leu Gln Val Ala His Ser Ala Pro Val Gly Ala Gln Leu Ala Thr Glu
            325                 330                 335
Leu Ser Ile Ala Glu Gly Gln Glu Val Leu Phe Gly Val Phe Val Thr
            340                 345                 350
Gly Lys Asp Gly Gly Pro Gly Val Gly Pro Asn Ser Val Val Cys Ala
            355                 360                 365
Phe Pro Ile Asp Leu Leu Asp Thr Leu Ile Asp Glu Gly Val Glu Arg
            370                 375                 380
Cys Cys Glu Ser Pro Val His Pro Gly Leu Arg Arg Gly Leu Asp Phe
385                 390                 395                 400
Phe Gln Ser Pro Ser Phe Cys Pro Asn Pro Pro Gly Leu Glu Ala Leu
                405                 410                 415
Ser Pro Asn Thr Ser Cys Arg His Phe Pro Leu Leu Val Ser Ser Ser
            420                 425                 430
Phe Ser Arg Val Asp Leu Phe Asn Gly Leu Leu Gly Pro Val Gln Val
            435                 440                 445
Thr Ala Leu Tyr Val Thr Arg Leu Asp Asn Val Thr Val Ala His Met
450                 455                 460
Gly Thr Met Asp Gly Arg Ile Leu Gln Val Glu Leu Val Arg Ser Leu
465                 470                 475                 480
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
            500                 505                 510
Ser Gly Asp Gln Val Phe Gln Val Pro Ile Arg Gly Pro Gly Cys Arg
            515                 520                 525
His Phe Leu Thr Cys Gly Arg Cys Leu Arg Ala Trp His Phe Met Gly
            530                 535                 540
Cys Gly Trp Cys Gly Asn Met Cys Gly Gln Gln Lys Glu Cys Pro Gly
545                 550                 555                 560
```

```
                                 -continued

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
                965                 970                 975
```

-continued

Val Phe Ser Tyr Trp Trp Arg Arg Lys Gln Leu Val Leu Pro Pro Asn
        980                 985                 990

Leu Asn Asp Leu Ala Ser Leu Asp Gln Thr Ala Gly Ala Thr Pro Leu
        995                 1000                1005

Pro Ile Leu Tyr Ser Gly Ser Asp Tyr Arg Ser Gly Leu Ala Leu
    1010                1015                1020

Pro Ala Ile Asp Gly Leu Asp Ser Thr Thr Cys Val His Gly Ala
    1025                1030                1035

Ser Phe Ser Asp Ser Glu Asp Glu Ser Cys Val Pro Leu Leu Arg
    1040                1045                1050

Lys Glu Ser Ile Gln Leu Arg Asp Leu Asp Ser Ala Leu Leu Ala
    1055                1060                1065

Glu Val Lys Asp Val Leu Ile Pro His Glu Arg Val Val Thr His
    1070                1075                1080

Ser Asp Arg Val Ile Gly Lys Gly His Phe Gly Val Val Tyr His
    1085                1090                1095

Gly Glu Tyr Ile Asp Gln Ala Gln Asn Arg Ile Gln Cys Ala Ile
    1100                1105                1110

Lys Ser Leu Ser Arg Ile Thr Glu Met Gln Gln Val Glu Ala Phe
    1115                1120                1125

Leu Arg Glu Gly Leu Leu Met Arg Gly Leu Asn His Pro Asn Val
    1130                1135                1140

Leu Ala Leu Ile Gly Ile Met Leu Pro Pro Glu Gly Leu Pro His
    1145                1150                1155

Val Leu Leu Pro Tyr Met Cys His Gly Asp Leu Leu Gln Phe Ile
    1160                1165                1170

Arg Ser Pro Gln Arg Asn Pro Thr Val Lys Asp Leu Ile Ser Phe
    1175                1180                1185

Gly Leu Gln Val Ala Arg Gly Met Glu Tyr Leu Ala Glu Gln Lys
    1190                1195                1200

Phe Val His Arg Asp Leu Ala Ala Arg Asn Cys Met Leu Asp Glu
    1205                1210                1215

Ser Phe Thr Val Lys Val Ala Asp Phe Gly Leu Ala Arg Asp Ile
    1220                1225                1230

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260

Phe Thr Thr Lys Ser Asp Val Trp Ser Phe Gly Val Leu Leu Trp
    1265                1270                1275

Glu Leu Leu Thr Arg Gly Ala Pro Pro Tyr Arg His Ile Asp Pro
    1280                1285                1290

Phe Asp Leu Thr His Phe Leu Ala Gln Gly Arg Arg Leu Pro Gln
    1295                1300                1305

Pro Glu Tyr Cys Pro Asp Ser Leu Tyr Gln Val Met Gln Gln Cys
    1310                1315                1320

Trp Glu Ala Asp Pro Ala Val Arg Pro Thr Phe Arg Val Leu Val
    1325                1330                1335

Gly Glu Val Glu Gln Ile Val Ser Ala Leu Leu Gly Asp His Tyr
    1340                1345                1350

Val Gln Leu Pro Ala Thr Tyr Met Asn Leu Gly Pro Ser Thr Ser
    1355                1360                1365

His Glu Met Asn Val Arg Pro Glu Gln Pro Gln Phe Ser Pro Met

```
      1370                1375                1380
Pro Gly Asn Val Arg Arg Pro  Arg Pro Leu Ser Glu  Pro Pro Arg
        1385                1390                 1395

Pro Thr
    1400

<210> SEQ ID NO 5
<211> LENGTH: 40
<212> TYPE: DNA
<213> ORGANISM: Homo sapiens

<400> SEQUENCE: 5
atgtggcaga tgctgaagag caactgctgc catggactca                              40

<210> SEQ ID NO 6
<211> LENGTH: 40
<212> TYPE: DNA
<213> ORGANISM: Homo sapiens

<400> SEQUENCE: 6
agaaagacta cgtacggacc cgggaggccg cgtgtgtctg                              40

<210> SEQ ID NO 7
<211> LENGTH: 40
<212> TYPE: DNA
<213> ORGANISM: Homo sapiens

<400> SEQUENCE: 7
gctgcggcat caaatcctgc gggtccgagg cacagccccg                              40

<210> SEQ ID NO 8
<211> LENGTH: 40
<212> TYPE: DNA
<213> ORGANISM: Homo sapiens

<400> SEQUENCE: 8
aagaggccac aactgtcagc acagacgacg tgcggcccca                              40

<210> SEQ ID NO 9
<211> LENGTH: 40
<212> TYPE: DNA
<213> ORGANISM: Homo sapiens

<400> SEQUENCE: 9
acgacgtgcg gccccaggac gctgatgacc agccgccatc                              40

<210> SEQ ID NO 10
<211> LENGTH: 40
<212> TYPE: DNA
<213> ORGANISM: Homo sapiens

<400> SEQUENCE: 10
agaaagacta cgtacggacc gggtccgagg cacagccccg                              40

<210> SEQ ID NO 11
<211> LENGTH: 33
<212> TYPE: DNA
<213> ORGANISM: Homo sapiens

<400> SEQUENCE: 11
cgttccaagc tgcgctaggt ggttgggggc cat                                     33
```

```
<210> SEQ ID NO 12
<211> LENGTH: 33
<212> TYPE: DNA
<213> ORGANISM: Homo sapiens

<400> SEQUENCE: 12
gggtccgagg cacagtagcc ccgccaagag gcc                              33

<210> SEQ ID NO 13
<211> LENGTH: 33
<212> TYPE: DNA
<213> ORGANISM: Homo sapiens

<400> SEQUENCE: 13
cggcgttcca agctggaggt ggttgggggc cat                              33

<210> SEQ ID NO 14
<211> LENGTH: 39
<212> TYPE: DNA
<213> ORGANISM: Homo sapiens

<400> SEQUENCE: 14
ctggatcagc ggcgtatcga aggtcgcgtg gttgggggc                        39

<210> SEQ ID NO 15
<211> LENGTH: 39
<212> TYPE: DNA
<213> ORGANISM: Homo sapiens

<400> SEQUENCE: 15
ctggatcagc ggcgtctggt tccgcgcgtg gttgggggc                        39

<210> SEQ ID NO 16
<211> LENGTH: 30
<212> TYPE: DNA
<213> ORGANISM: Homo sapiens

<400> SEQUENCE: 16
ccagggaccc ctaagcattg agtcagaagc                                  30
```